: US 10,973,982 B2
(45) Date of Patent: Apr. 13, 2021

(12) United States Patent
Keating

(10) Patent No.: US 10,973,982 B2
(45) Date of Patent: Apr. 13, 2021

(54) METHOD AND SYSTEM FOR OPERATING A PLUNGER

(71) Applicant: Kellida Inc., Atlanta, GA (US)

(72) Inventor: Virginia Souris Keating, Atlanta, GA (US)

(73) Assignee: Kellida, Inc., Atlanta, GA (US)

( * ) Notice: Subject to any disclaimer, the term of this patent is extended or adjusted under 35 U.S.C. 154(b) by 0 days.

(21) Appl. No.: 16/827,433

(22) Filed: Mar. 23, 2020

(65) Prior Publication Data

US 2020/0254183 A1 Aug. 13, 2020

Related U.S. Application Data

(63) Continuation of application No. 16/392,458, filed on Apr. 23, 2019.

(60) Provisional application No. 62/661,122, filed on Apr. 23, 2018.

(51) Int. Cl.
*A61M 5/31* (2006.01)

(52) U.S. Cl.
CPC ........ *A61M 5/3137* (2013.01); *A61M 5/3135* (2013.01); *A61M 5/3148* (2013.01); *A61M 2005/3139* (2013.01)

(58) Field of Classification Search
CPC ........ A61M 5/3137; A61M 2005/3139; A61M 31/002; A61M 5/00; A61B 18/1815
See application file for complete search history.

(56) References Cited

U.S. PATENT DOCUMENTS

| 2,346,607 | A |   | 4/1944 | Raiman |   |
|---|---|---|---|---|---|
| 2,842,128 | A | * | 7/1958 | Hein, Jr. | A61M 5/31 604/227 |
| 3,758,006 | A | * | 9/1973 | Gravlee | A61M 5/178 222/323 |
| D248,598 | S |   | 7/1978 | Bahmer |   |
| 4,217,896 | A | * | 8/1980 | Behnke | A61M 5/3148 604/227 |
| 4,324,241 | A | * | 4/1982 | Reese | A61M 5/31 604/227 |
| 4,351,334 | A | * | 9/1982 | Inglefield, Jr. | A61M 5/3148 604/227 |

(Continued)

FOREIGN PATENT DOCUMENTS

WO 9822166 A1 5/1998

OTHER PUBLICATIONS

Miltex, Dental Syringes and Accessories, 2010, 6 pages, Integra LifeSciences Corporation (brochure).

(Continued)

*Primary Examiner* — Scott J Medway

(57) ABSTRACT

An apparatus can aid usage of a plunger, for example helping a medical practitioner use a hypodermic syringe to inject dermal filler. The apparatus can fasten a thumb rest of a plunger of the syringe to a thumb of the practitioner and can support one-handed operation of the syringe. With the plunger so fastened, reverse thumb motion can retract the plunger for aspiration, and forward thumb motion can advance the plunger for injection. The apparatus can comprise a member extending at least partially around the practitioner's thumb. The member can comprise an aperture configured to retain the thumb rest between the thumb and the member, with a shaft of the plunger passing through the aperture.

17 Claims, 11 Drawing Sheets

(56) References Cited

U.S. PATENT DOCUMENTS

| | | | | |
|---|---|---|---|---|
| 4,687,472 | A * | 8/1987 | Gross | A61M 5/24 604/223 |
| 5,046,381 | A * | 9/1991 | Mueller | G05G 1/06 74/558 |
| 5,129,888 | A * | 7/1992 | Bidoia | A61M 5/347 600/576 |
| D335,196 | S | 4/1993 | Lamb et al. | |
| 5,554,132 | A * | 9/1996 | Straits | A61M 5/31511 604/187 |
| 5,556,092 | A * | 9/1996 | Theken | A63B 60/10 473/538 |
| D397,790 | S | 9/1998 | Naganuma | |
| 5,833,668 | A * | 11/1998 | Aguilar | A61M 5/3135 604/227 |
| 6,068,616 | A * | 5/2000 | Janus | A61M 5/24 604/187 |
| D434,850 | S | 12/2000 | Balestracci | |
| D465,306 | S | 11/2002 | Price | |
| D504,635 | S | 5/2005 | Jones | |
| 6,944,914 | B2 * | 9/2005 | Tillim | A61B 17/2909 16/430 |
| D543,625 | S | 5/2007 | Numata et al. | |
| 7,364,570 | B2 | 4/2008 | Gerondale et al. | |
| D620,384 | S | 7/2010 | Crovetti | |
| D675,317 | S | 1/2013 | Baxter et al. | |
| D702,402 | S | 4/2014 | Pew | |
| D750,768 | S | 3/2016 | Davidian et al. | |
| D790,691 | S | 6/2017 | Davis et al. | |
| D794,185 | S | 8/2017 | Dolk et al. | |
| D794,187 | S | 8/2017 | Dolk et al. | |
| D797,282 | S | 9/2017 | Dolk et al. | |
| D811,589 | S | 2/2018 | Finke et al. | |
| D812,223 | S | 3/2018 | Evans et al. | |
| D814,630 | S | 4/2018 | Finke et al. | |
| D823,836 | S | 7/2018 | Eaton | |
| D830,220 | S | 10/2018 | Hardy | |
| 10,124,238 | B2 * | 11/2018 | McCrane | A63B 21/4035 |
| D842,751 | S | 3/2019 | Hardy | |
| D844,776 | S | 4/2019 | Combes et al. | |
| D865,950 | S | 11/2019 | Mandaroux et al. | |
| D869,775 | S | 12/2019 | Voosen | |
| 2003/0028146 | A1 * | 2/2003 | Aves | A61N 1/0551 604/164.06 |
| 2005/0209571 | A1 * | 9/2005 | McKay | A61M 5/3148 604/227 |
| 2006/0205526 | A1 * | 9/2006 | Whitehead, II | A63B 71/148 473/59 |
| 2009/0093787 | A1 * | 4/2009 | Barbour | A61M 5/3137 604/506 |
| 2012/0220948 | A1 | 8/2012 | Barbour | |
| 2015/0238698 | A1 | 8/2015 | Perry et al. | |
| 2017/0119952 | A1 * | 5/2017 | Wen | A61M 5/3137 |
| 2019/0030253 | A1 * | 1/2019 | Barbour | A61M 5/3148 |
| 2020/0206425 | A1 | 7/2020 | Keating | |

OTHER PUBLICATIONS

Medestheticsmag.com, Jan. 12, 2017, 1 page.
Angiographic Control Syringes, Namic Fluid Management, 2014, 4 pages, AngioDynamics, Inc.
Lee, Preventing Catastrophes—While Injecting Facial Wrinkles, Oct. 21, 2016, 2 pages, Press Advantage.
ProSystem Bionic Oxygen Recovery, Prime-Journal.com, Jul./Aug. 2017, 2 pages.
Jireis, The Best Guitar Finger Picks by Dunlop—Thumbpicks Included! Jan. 7, 2017, 2 pages.
Sibbitt et al., Thyroid Biopsy with the Reciprocating Procedure Device (RPD), 2006, 2007, 114 pages, University of New Mexico Health Sciences Center.
EP 20170359.2, European Search Report dated Jun. 3, 2020, 8 pages.
Notice of Allowance issued in U.S. Appl. No. 29/688,668, dated Jul. 29, 2020, 26 pages.

* cited by examiner

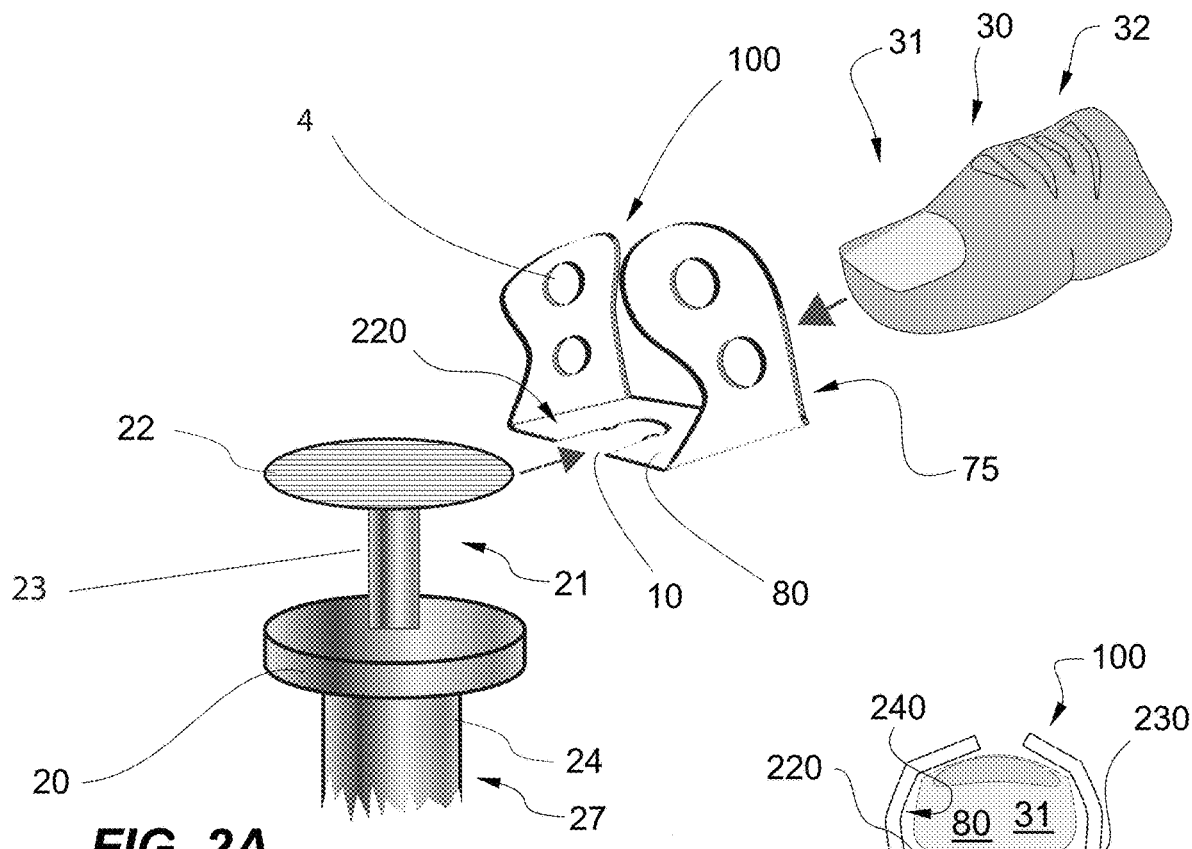
*FIG. 2A*
*FIG. 2B*
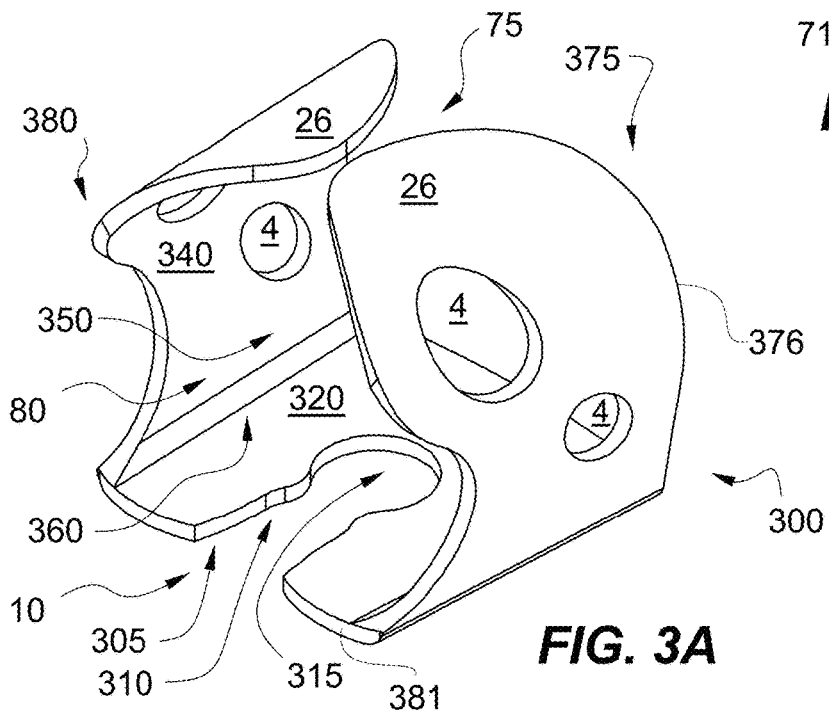
*FIG. 3A*

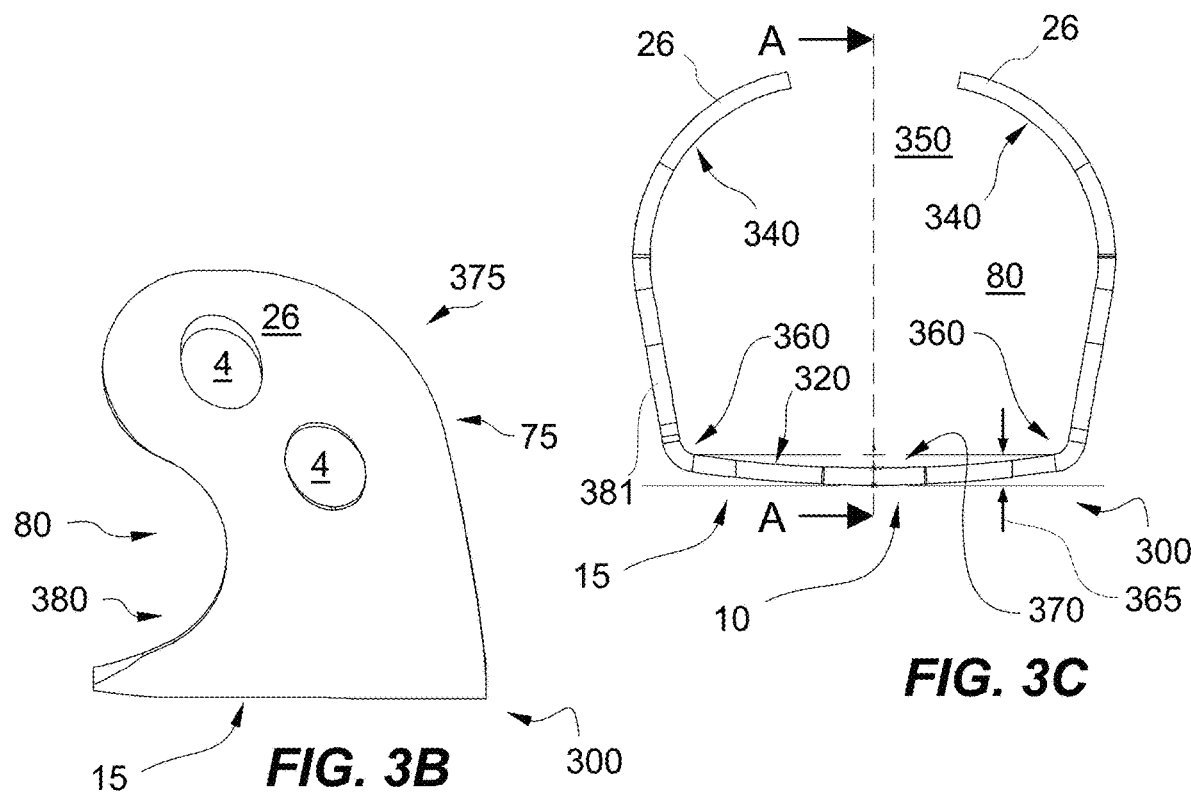
FIG. 3B
FIG. 3C
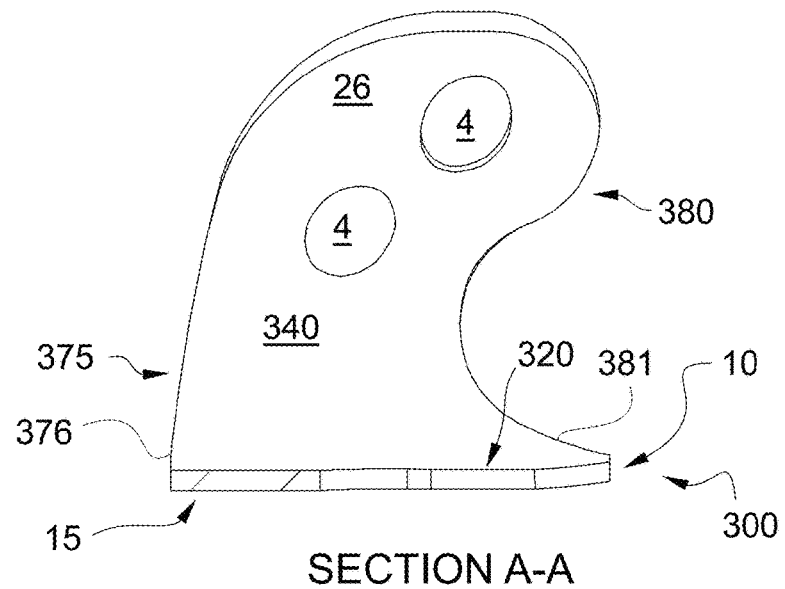
SECTION A-A
FIG. 3D

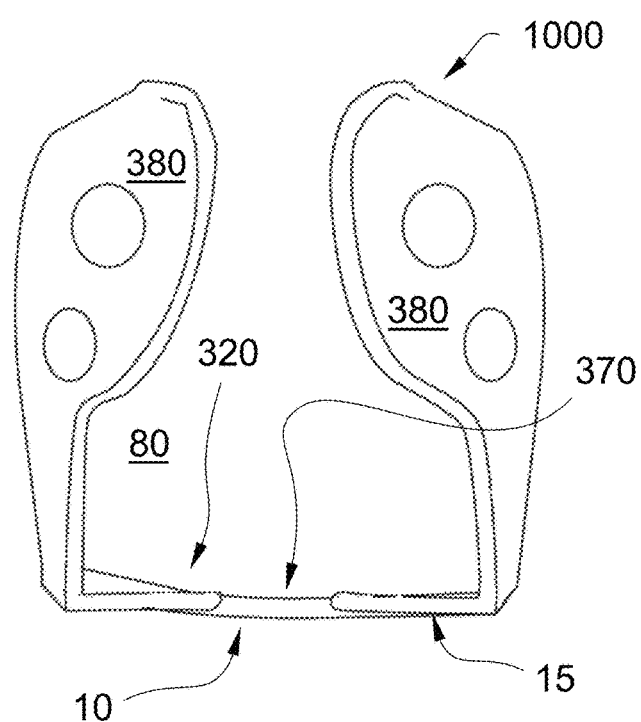 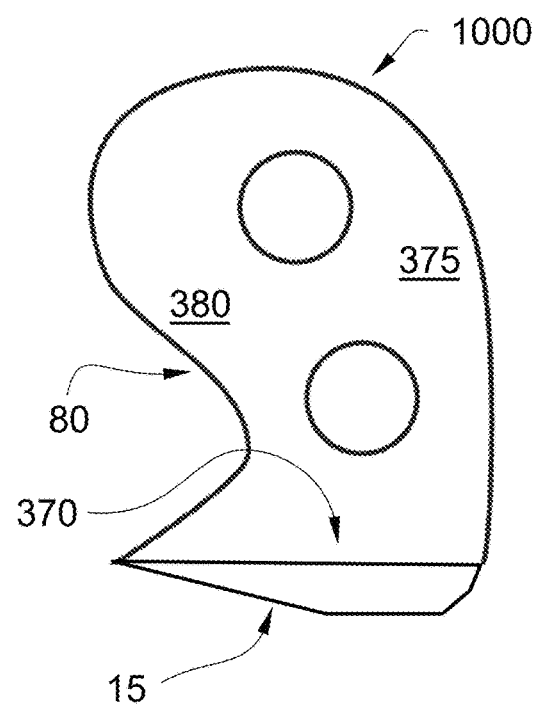
FIG. 10A   FIG. 10B
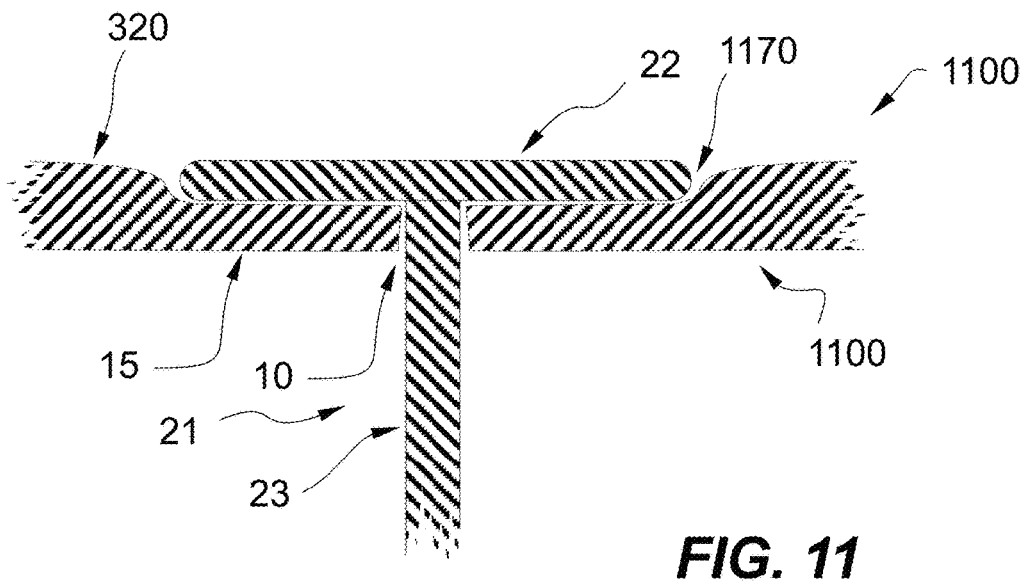
FIG. 11

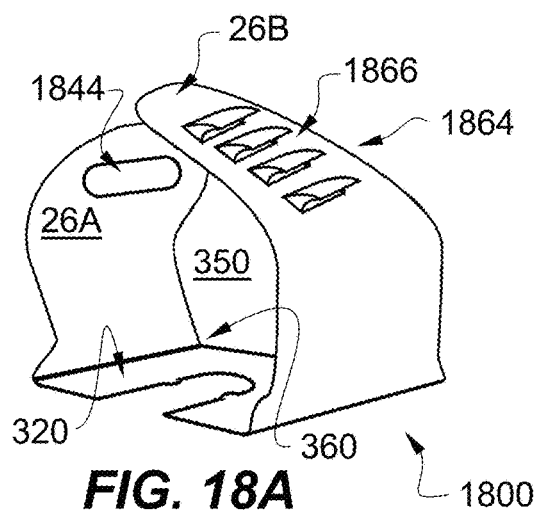
FIG. 18A
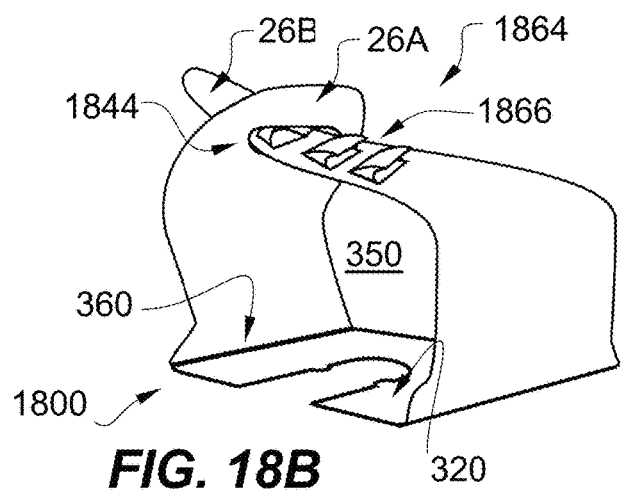
FIG. 18B
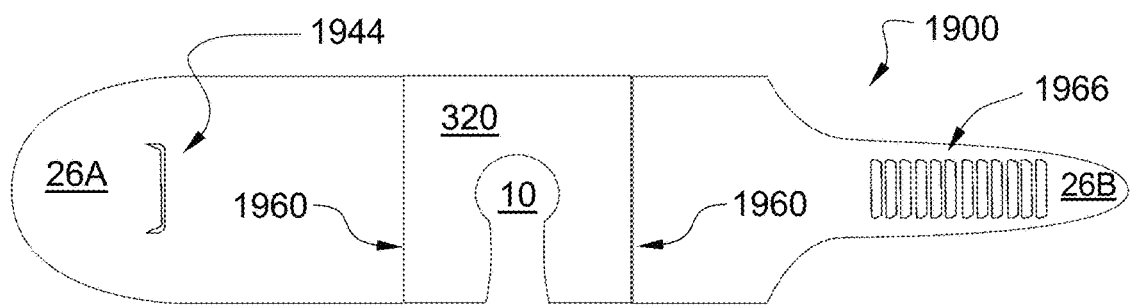
FIG. 19
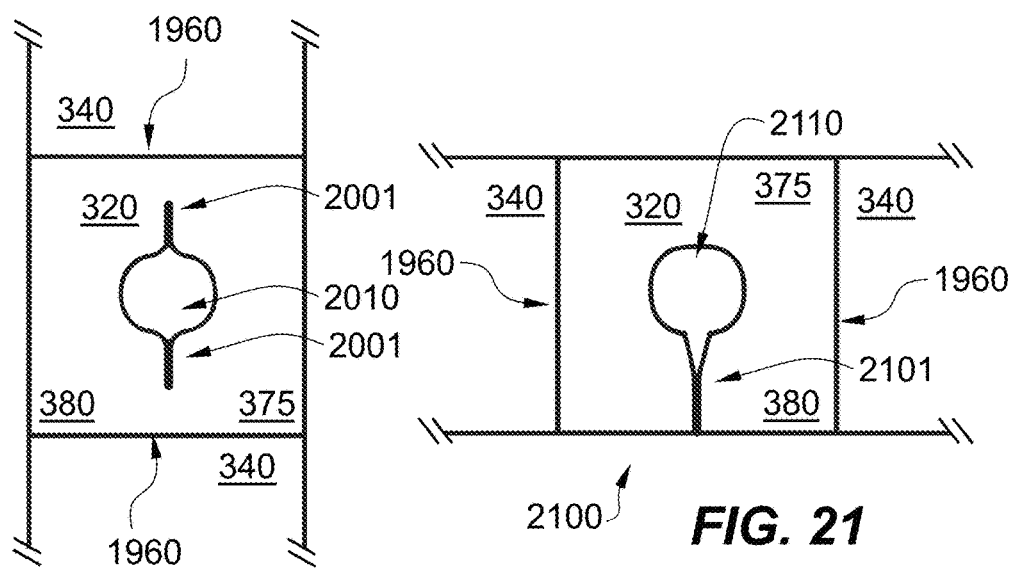
FIG. 20
FIG. 21

METHOD AND SYSTEM FOR OPERATING A PLUNGER

CROSS REFERENCE TO RELATED APPLICATIONS

This application claims priority to co-pending U.S. patent application Ser. No. 16/392,458 filed Apr. 23, 2019 in the name of Virginia Souris Keating and entitled "Method and System for Operating a Plunger," which claims priority to U.S. Provisional Patent Application No. 62/661,122 filed Apr. 23, 2018 in the name of Virginia Souris Keating and entitled "Novel Adjustable Clip-on Ring to Aid in Injection and Aspiration of a Syringe." The entire contents of each of the above-identified applications, including U.S. patent application Ser. Nos. 16/392,458 and 62/661,122, are hereby incorporated herein by reference. This application is related to U.S. Design patent application No. 29/688,668, filed on Apr. 23, 2019 under docket number KELL 1145.1001.D1 in the name of Virginia Souris Keating and entitled "Plunger Fastening Device," the entire contents of which are hereby incorporated herein by reference.

TECHNICAL FIELD

Embodiments of the technology relate generally to operating a plunger, and more specifically to fastening the plunger to a user to improve dexterity of operation, for example supporting precision retraction of a plunger of a hypodermic syringe in connection with aspirating the syringe.

BACKGROUND

Operators of devices that comprise plungers have often faced limitations in the level of precision with which they can move or position a plunger. For example, to achieve adequate plunger control using conventional approaches, an operator may find need to hold the device with one hand and retract the plunger with the other hand.

There is a deficiency in the art for technology for moving a plunger. Need exists for an improved capability to operate a plunger with precision. Need further exists for an improved capability to move a plunger manually with dexterity. Need further exists to improve retraction of plungers of medical instruments and tools. Need further exists to improve retraction of plungers of industrial instruments and tools. Need further exists for an improved capability for one-handed operation of a device that comprises a plunger. Need further exists for an improved capability for aspirating a hypodermic syringe or other medical device comprising a plunger. Need further exists for an improved capability for retracting a plunger of a biopsy instrument. A technology addressing one or more such needs, or a related deficiency in the art, could improve usage of devices incorporating plungers.

SUMMARY

A method and system can assist with moving a plunger, for example improving dexterity for someone using a device comprising a plunger. The device can comprise an industrial device or a medical device, such as a biopsy device, a surgical instrument, or a hypodermic syringe.

In one aspect of the disclosure, fastening a plunger to its user can increase dexterity or precision with which the user can retract the plunger.

In one aspect of the disclosure, fastening a plunger to a thumb or other appropriate appendage of a user can offer the user a capability for one-handed retraction of the plunger.

In one aspect of the disclosure, a plunger of a syringe can comprise a flange, for example a thumb rest. A user can apply force to the flange to advance the plunger. Advancing the plunger can cause material to emit from the syringe, for example in connection with a medical practitioner injecting a substance into a patient during a medical procedure. The flange can be fastened to an appendage of the user, for example to the user's thumb. With the flange so fastened, the user can retract the plunger with finesse, for example in support of performing an aspiration associated with a hypodermic injection or other procedure.

The foregoing discussion about moving a plunger is for illustrative purposes only. Various aspects of the present disclosure may be more clearly understood and appreciated from a review of the following text and by reference to the associated drawings and the claims that follow. Other aspects, systems, methods, features, advantages, and objects of the present disclosure will become apparent to those with skill in the art upon examination of the following drawings and text. It is intended that all such aspects, systems, methods, features, advantages, and objects are to be included within this description and covered by this paper and by the appended claims.

BRIEF DESCRIPTION OF THE FIGURES

FIG. 1, are illustrations of a ring for fastening a plunger to a user, with the ring illustrated in a representative medical application, in accordance with some example embodiments of the disclosure.

FIGS. 2A and 2B, collectively FIG. 2, are illustrations of a ring for fastening a plunger to a user, depicting representative features of fastening in accordance with some example embodiments of the disclosure.

FIGS. 3A, 3B, 3C, and 3D, collectively FIG. 3, are illustrations of a ring for fastening a plunger to a user in accordance with some example embodiments of the disclosure.

FIG. 4, are illustrations of a blank to be formed into a ring for fastening a plunger to a user in accordance with some example embodiments of the disclosure.

FIG. 6, are illustrations of a ring for fastening a plunger to a user in accordance with some example embodiments of the disclosure.

FIG. 8, are illustrations of a ring for fastening a plunger to a user in accordance with some example embodiments of the disclosure.

FIGS. 10A and 10B, collectively FIG. 10, are illustrations of a ring for fastening a plunger to a user in accordance with some example embodiments of the disclosure.

FIG. 11 is an illustration of a portion of a ring for fastening a plunger to a user in accordance with some example embodiments of the disclosure.

FIGS. 18A and 18B, collectively FIG. 18, are illustrations of a ring for fastening a plunger to a user in accordance with some example embodiments of the disclosure.

FIG. 19 is an illustration of a ring for fastening a plunger to a user in accordance with some example embodiments of the disclosure.

FIG. 20 is an illustration of a portion of a ring for fastening a plunger to a user in accordance with some example embodiments of the disclosure.

FIG. 21 is an illustration of a portion of a ring for fastening a plunger to a user in accordance with some example embodiments of the disclosure.

FIG. 23, are illustrations of a ring for fastening a plunger to a user in accordance with some example embodiments of the disclosure.

Figures 1A, 1B:
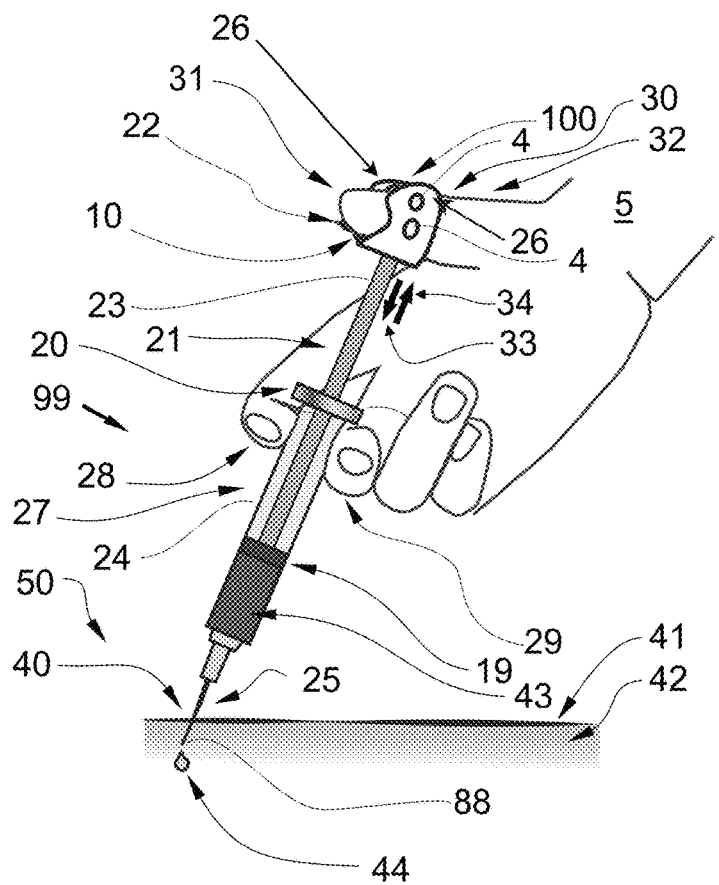
FIGS. 1A, 1B, 1C, and 1D, collectively

Many aspects of the disclosure can be better understood with reference to these figures. The elements and features shown in the figures are not necessarily to scale, emphasis being placed upon clearly illustrating the principles of example embodiments of the disclosure. Moreover, certain dimensions may be exaggerated to help visually convey such principles. In the figures, reference numerals often designate like or corresponding, but not necessarily identical, elements throughout the several views.

DETAILED DESCRIPTION OF EXAMPLE EMBODIMENTS

The technology will be discussed more fully hereinafter with reference to the Figures, which provide additional information regarding representative or illustrative embodiments of the disclosure. FIG. 1 provides, inter alia, disclosure relevant to using a ring in a representative application of performing a hypodermic injection. FIG. 2 provides, inter alia, disclosure relevant to a user representatively donning a ring. FIGS. 3, 4, 5, 6, 7, 8, 9, 10, 11, 12, 13, 14, 15, 16, 17, 18, 19, 20, 21, 22, 23, and 24 provide, inter alia, disclosure relevant to representative ring features. FIG. 24 provides, inter alia, disclosure relevant to methods or processes involving a ring.

The present technology can be embodied in many different forms and should not be construed as limited to the embodiments set forth herein; rather, these embodiments are provided so that this disclosure will be thorough and complete, and will fully convey the scope of the technology to those having ordinary skill in the art. Furthermore, all "examples," "embodiments," and "exemplary embodiments" provided herein are intended to be non-limiting, and among others supported by representations of the disclosure.

Those of ordinary skill in the art having benefit of this disclosure will be able, without undue experimentation, to combine compatible elements and features that are described in detail at various places in this written description, which includes text and illustrations. That is, the illustrations and specification are organized to facilitate practicing numerous combinations, such as combining an element of one illustrated embodiment with another element of another illustrated embodiment.

This document includes sentences, paragraphs, and passages (some of which might be viewed as lists) disclosing alternative components, elements, features, functionalities, usages, operations, steps, etc. for various embodiments of the disclosure. Unless clearly stated otherwise, all such lists, sentences, paragraphs, passages, and other text are not exhaustive, are not limiting, are provided in the context of describing representative examples and variations, and are among others supported by various embodiments of the disclosure. Accordingly, those of ordinary skill in the art having benefit of this disclosure will appreciate that the disclosure is not constrained by any such lists, examples, or alternatives. Moreover, the inclusion of lists, examples, embodiments, and the like (where provided) may help guide those of ordinary skill in practicing many more implementations and instances that embody the technology without undue experimentation, all of which are intended to be within the scope of the claims.

This disclosure includes figures and discussion in which features and elements of certain embodiments may be organized into what might be characterized as functional units, blocks, subsystems, or modules. And, certain processes and methods may be organized into blocks or into steps. Such organization is intended to enhance readership and to facilitate teaching the reader about working principles of the technology and about making and using an abundance of embodiments of the disclosure. The organization is not intended to force any rigid divisions or partitions that would limit the disclosure. In practice, the flexibility of the technology and the depth of this disclosure supports dispersing or grouping functionalities, elements, and features in many different ways. The inclusion of an element or function in one block, unit, module, or subsystem verses another may be substantially arbitrary in many instances, with the divisions being soft and readily redrawn using ordinary skill and this rich teaching. Accordingly, functional blocks, modules, subsystems, units, and the like can be combined, divided, repartitioned, redrawn, moved, reorganized, or otherwise altered without deviating from the scope and spirit of the disclosure. This is not to say that, nor will it support a conclusion that, any disclosed organizations and combinations are not novel, are not innovative, or are obvious.

The term "plunger," as used herein, generally refers to an elongate component that moves lengthwise in an elongate cavity, often in connection with moving matter into or out of the cavity. For example, a plunger may advance in a barrel of a hydraulic device to move matter out of the barrel or retract from the barrel to move matter out of the cylinder.

The term "fasten," as used herein, generally refers to physically coupling something to something else firmly or securely.

The term "fastener," as may be used herein, generally refers to an apparatus or system that fastens something to something else, whether releasably, temporarily, or permanently.

The term "couple," as may be used herein, generally refers to joining, connecting, or associating something with something else.

As one of ordinary skill in the art will appreciate, the term "operably coupled," as may be used herein, encompasses direct coupling and indirect coupling via another, intervening component, element, circuit, or module; moreover, a first component may be operably coupled to a second component when the first component comprises the second component.

The term "slot," as used herein, generally refers to an elongate aperture.

The term "palmar surface," as may be used herein with reference to a finger, a thumb, or a hand, generally refers to the surface of the finger, the thumb, or the hand located on the same side as the palm.

The term "friction ridge region," as may be used herein, generally refers to a region of the human anatomy that has friction ridges or epidermal ridges, such as the region of a thumb that leaves fingerprints.

As one of ordinary skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, process variations, and manufacturing tolerance.

Turning now to FIGS. 1A, 1B, 1C, and 1D, these figures illustrate an example ring 100 fastening an example plunger 21 to an example user 5 in an example medical application according to some embodiments of the disclosure. In the illustrated embodiment of FIG. 1, the plunger 21 is a component of a syringe 27, which in this example comprises a hypodermic syringe containing a material 43 to be injected. Thus, a system 99 comprising the ring 100, the syringe 27, and a material 43 is illustrated. As discussed in further detail below, in the illustrated example application, the ring 100 (among other capabilities) facilitates performing an aspiration to avoid inadvertent delivery of injected material 44 into a vascular lumen of a vein or artery (not illustrated).

In the illustrated embodiment, the syringe 27 comprises a barrel 24 and a finger flange 20, with the plunger 21 extending from the barrel 24 opposite a needle 25. The barrel 24 houses the material 43 to be injected. The example plunger 21 of the illustrated syringe 27 comprises a plunger head 19 that may have an elastomeric composition (for example synthetic rubber) for sealing the material 43 in the barrel 24. The plunger 21 further comprises a shaft 23 that extends out of the barrel 24 to a flange 22 that may comprise a thumb rest in some example embodiments. The flange 22 is disposed between a ring 100 and a thumb 30 of the user 5, with the shaft 23 extending through a slot 10 in the ring 100. In the example embodiment of FIG. 1, the ring 100 fastens the plunger 21 to the user's thumb 30. In some example embodiments, the ring 100 can be characterized as a fastener.

As illustrated, the example ring 100 comprises ends 26 that extend partially or fully about the thumb 30 and may extend past one another adjacent the user's thumbnail in some embodiments. In some example embodiments, the ends 26 extend at least half way around the thumb 30 and embrace the thumb 30. Thus, the ring 100 may fully or partially circumscribe the thumb 30, with 360 degrees of extension, less than 360 degrees of extension, or more than 360 degrees of extension.

As illustrated, the ends 26 comprise apertures 4, as will be discussed in further detail below. As illustrated, a distal portion 31 of the thumb 30 extends out of a distal opening 80 of the ring 100, and a proximal portion 32 of the thumb 30 extends out of a proximal opening 75 of the ring 100.

In operation, in the example illustrated in FIG. 1, the barrel 24 is disposed between the middle finger 29 and index finger 28 of the user 5, adjacent the finger flange 20 of the syringe 27. The user 5 can move his or her thumb 30 upward 34 along the axis 90 and away from the finger flange 20 and the index and middle fingers 28 and 29 to produce a retracting motion 36 of the plunger 21. Thus, a lower exterior surface 15 of the ring 100 and the plunger flange 22 (captured in the ring 100) move away from the finger flange 22. The index and middle fingers 28 and 29 can be situated above and below the finger flange 20 during retraction, for example. As discussed in further detail below with reference to FIG. 25, precision retraction and/or one-handed retraction of the plunger 21 can be useful for (among other things) performing an aspiration prior to injecting the material 43 in tissue 42 below the surface of the skin 41 at the injection site 40 of a patient 50. In some embodiments, the injection site 40 comprises a facial area of the patient 50, and FIG. 1 illustrates a facial filler injection. The patient 50 can comprise a human or a non-human animal or other appropriate subject. In some examples, a subject may be or comprise an inanimate object.

The user 5 can move his or her thumb downward 33 along the axis 90, towards the finger flange 20 and the index and middle fingers 28 and 29, to produce an advancing motion 35 of the plunger 21. Thus, the lower exterior surface 15 of the ring 100 and the plunger flange 22 move in unison towards the finger flange 20. Advancing the plunger 21 can cause delivery of the material 43 through a distal port 88 of the needle 44.

Figure 1C:
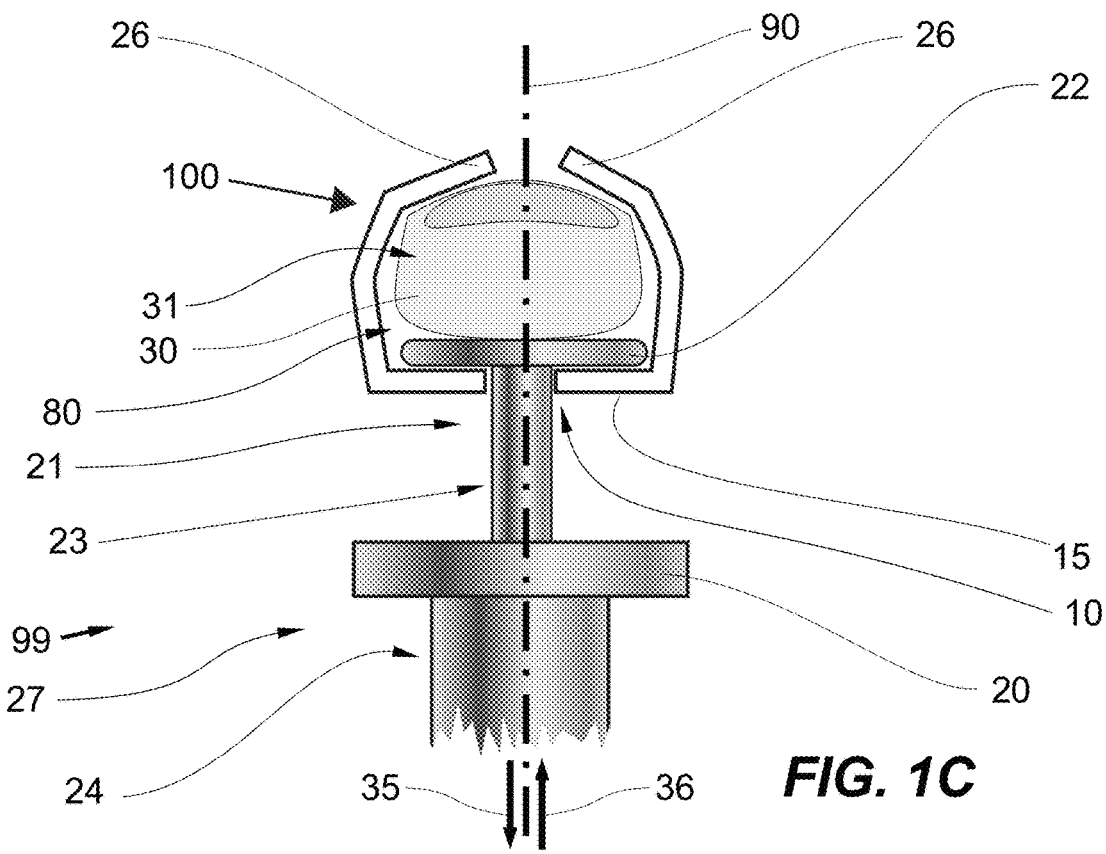
Figure 1D:
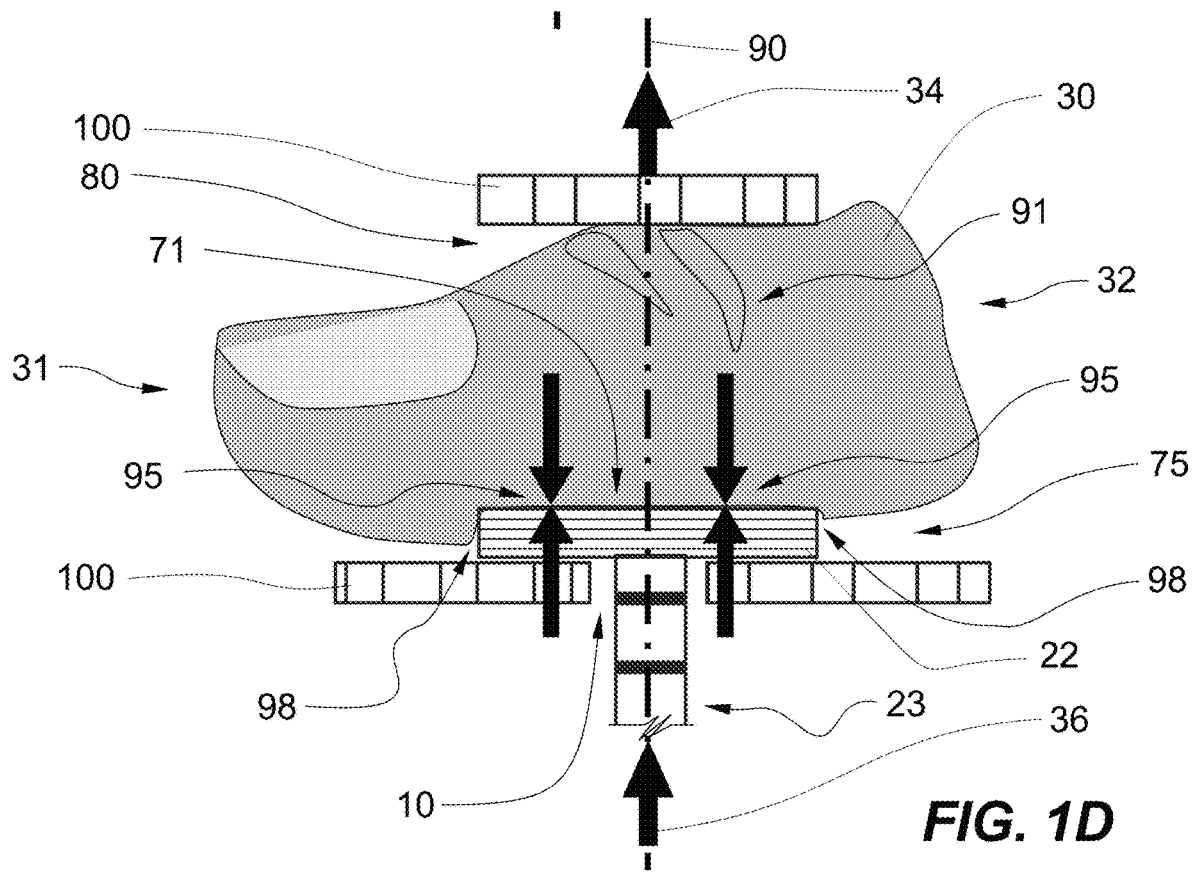

Referring now to FIG. 1D, the interphalangeal joint 91 of the user's thumb 30 (the most distal joint) can be positioned on the axis 90 in some example embodiments. (In some embodiments, the user 5 may prefer more distal or more proximal ring positioning than illustrated in FIG. 1D.) Throughout upward motion 34 of the user's thumb 30 and retraction 36 of the plunger 21, the plunger flange 22 and the thumb 30 can exert force 95 upon one another. As illustrated, the flange 22 can apply force 95 to the lower surface 71 of the thumb 30 during the entire time of a plunger retraction 36, and the force 95 can produce deformation of and a depression 98 in the lower surface 71 of the thumb 30. Thus, while the thumb 30 is lifting up, the flange 22 continues to exert force 95 on the lower surface 71 of the thumb 30 (and the lower surface 71 of the thumb 30 continues to exert force 95 on the flange 22.

Beyond assisting in retracting the plunger to avoid injecting in a vascular lumen, the ring 100 can be utilized to help position a distal port 88 of the needle 40 in a vascular lumen. For example, when drawing blood from a vascular lumen, injecting intravenously, or placing a catheter in a vascular lumen, the user 5 can retract the plunger 21 and look for aspirated blood as confirmation that the needle 40 is in the vascular lumen. Moreover, the ring 100 can increase dexterity of withdrawing fluids or aspiration in various medical and veterinary applications.

The user 5 can comprise a medical practitioner, for example a physician's assistant, a nurse, a physician, a technician, a nurse practitioner, a biomedical researcher, or other appropriate person. The user 5 can further comprise a person working in the veterinary field. In some embodiments, the user 5 can further comprise a person working in an industrial or nonmedical field.

The ring 100 can further heighten dexterity for retracting a plunger 21 or similar member using a biopsy device. Planes of injection (or of other intervention) can include subdermal, subcutaneous, intra muscular, intra vascular, peri osteo, and intraspinal forms, to mention some representative examples without limitation.

In some example embodiments, the material 43 comprises a dermal filler, such as the commercial dermal filler products marketed by Allergan under the registered trade names of "JUVEDERM," "VOLUMA," "VOLBNELLA," OR "VOLLURE;" by Galderma under the registered trade names of "RESTYLANE" AND "SCULPTRA"; by Merz under the registered trade names of "RADIESSE", and BELOTERO; or by Suneva under the registered trade name of "BELLAFIL." In some example embodiments, the material comprises a dermal filler that comprises hyaluronic acid, calcium hydroxyapatite (CaHA) gel, poly-L-lactic acid fluid, injectable bovine collagen, or non-resorbable polymethylmethacrylate (PMMA) (not an exhaustive list).

Various other materials 43 to be injected may be housed in the barrel 24, such as medical agents intended for intramuscular delivery, for subcutaneous injection, or for intradermal injection, for example. Materials that may be delivered via intramuscular injection may include paliperidone, chlorpromazine, dimercaprol, ketamine, leuprorelin, naloxone, quinine, lorazepam, vaccines (e.g., rabies, hepatitis A, gardasil, influenza), fulvestrant, codeine, morphine, methotrexate, metoclopramide, olanzapine, streptomycin, diazepam, prednisone, antibiotics (e.g., penicillin), haloperidol, aripiprazole, interferon beta-la, sex hormones, vitamin B12, risperidone, and platelet-rich plasma, to mention a few representative examples without limitation.

In some examples, a pharmaceutical company provides the syringe 27 prefilled with the material 43 to be injected. In other examples, the user 5 loads the material 43 into the syringe 27 at a point of care.

Turning now to FIGS. 2A and 2B, these figures illustrate example features of fastening a plunger 21 to a user 5 with a ring 100 according to some embodiments of the disclosure. FIG. 2A describes an example way of donning the ring 100. In the illustrated example, the plunger 21 is an element of a syringe 27 that comprises a barrel 24 and a finger flange 20 consistent with the foregoing discussion of FIG. 1.

As illustrated, the user 5 inserts the distal portion 31 of his or her thumb 30 into the proximal opening 75 of the ring 100 and inserts the shaft 23 of the plunger 21 into the slot 10 of the ring. Consequently, the flange 22 of the plunger 21 may be disposed between the user's thumb 30 and the floor 220 of the ring 100, with the shaft 23 of the plunger 21 extending through the slot 10, for example as illustrated at FIG. 1C. The distal portion 31 of the user's thumb 30 may extend out of the distal opening 80 of the ring, and the proximal portion 32 of the user's thumb 30 may extend out of the proximal opening 75 of the ring 100.

In some example embodiments, the user's thumb 30 is inserted into the proximal opening 75 and the plunger shaft 23 is inserted in the slot 10 so that the two insertions occur concurrently or during overlapping timeframes. In some example embodiments, the user 5 first inserts the plunger shaft 23 into the slot 10, and then the user 5 inserts his or her thumb 30 into the ring 100. In some example embodiments, the user 5 first inserts his or her thumb 30 into the ring 100, and then inserts the plunger shaft 23 into the slot 10. In some example embodiments, the user 5 inserts his or her thumb 30 partially into the ring 100, then inserts the plunger shaft 23 into the slot 10, and then pushes his or her thumb 30 further into the ring 100 until there is a tight fit.

As illustrated in FIG. 2B, a gap 230 can exist between the floor 220 of the ring 100 and the lower surface 71 of the thumb 30. In some example embodiments, the lower surface 71 of the thumb 30 can comprise a friction ridge region of the thumb 30 or a palmar surface of the thumb 30.

The plunger 21 can take up the gap 230 so that the user 5 can maintain pressure on the plunger flange 22 during retraction of the plunger 21, for example. Reducing or eliminating the gap 230 can reduce backlash or play during plunger operation in some example embodiments.

FIG. 2B further illustrates how the contours of the thumb 30 can follow or match the contours of the interior side surface 240 and the floor 220 of the ring 100. The like contours can promote a snug fit in some embodiments, for example.

In some example embodiments, apertures 4 can help avoid suction between the ring 100 and a medical glove (not illustrated) covering the thumb 30 while the user 5 is putting the ring 100 on or taking the ring 100 off. In some example embodiments, the apertures 4 can help hold the ring 100 on the user's thumb 30, as a result of increased friction at the peripheral edges of the apertures 4 or from the user's glove or thumb skin protruding slightly into the apertures 4. In some example embodiments, the apertures 4 support aesthetics and further may provide a receptacle for mounting a gem stone or other personalizing element.

Turning now to FIGS. 3A, 3B, 3C, and 3D, these figures illustrate an example ring 300 for fastening a plunger 21 to a user 5 according to some embodiments of the disclosure. The ring 300 illustrated in FIG. 3 represents an example embodiment of the ring 100 illustrated in FIGS. 1 and 2 and discussed above. The views of FIG. 3 illustrate example contours and features of an example embodiment in further detail as may be desirable in some applications, including from the perspectives of ergonomics and heightened precision and dexterity, for example. FIG. 3A illustrates a perspective view. FIG. 3B illustrates a side view FIG. 3C illustrates an end view. FIG. 3D illustrates a cross sectional view, with the cross section taken on the cut plane indicated in FIG. 3C.

The example ring 300 comprises a distal opening 80 with an associated distal edge 381 and a distal portion 380. A slot 10 extends into a floor 320 of the ring 300. The slot 10 comprises a mouth 305, a middle region 310, and a rear region 315. In the illustrated embodiment, the middle region 310 is narrower than the mouth 305 and is narrower than the rear region 315. As illustrated, the rear region 315 comprises one example of a curved outline at a closed end of a slot 10. The slot 10 comprise a rim in some embodiments.

Longitudinally opposite from the distal opening 80, the example ring 300 comprises a proximal opening 75 with an associated proximal edge 376 and a proximal portion 375. The ring ends 26 extend upward from a floor 320 of the ring 300 and form a section that extends longitudinally between the distal opening 80 and the proximal opening 75 of the ring 300. This section may partially or fully circumscribe an interior space 350 of the ring 300. Interior surfaces 340 of the ring 300 and the floor 320 define an interior space 350. The ends 26 comprise apertures 4, further discussed below.

As best seen in FIG. 3C, the floor 320 sags or curves downward to provide a recessed space 370 below corners 360. The recessed space 370 can have a depth 365 that accommodates at least a portion of a thickness of the flange 22 to promote plunger seating and retention by the ring 300, for example. In some example embodiments, the floor 320 further curves downward in the longitudinal dimension (orthonormal to the view of FIG. 3C). For example, a portion of the floor 320 that adjoins the rear region 315 of the slot 10 may be sunk below distal and proximal portions of the floor. A portion of floor 320 may provide an interior surface that is concave or that is shaped like a bowl or a saddle in some example embodiments.

Figure 4A:
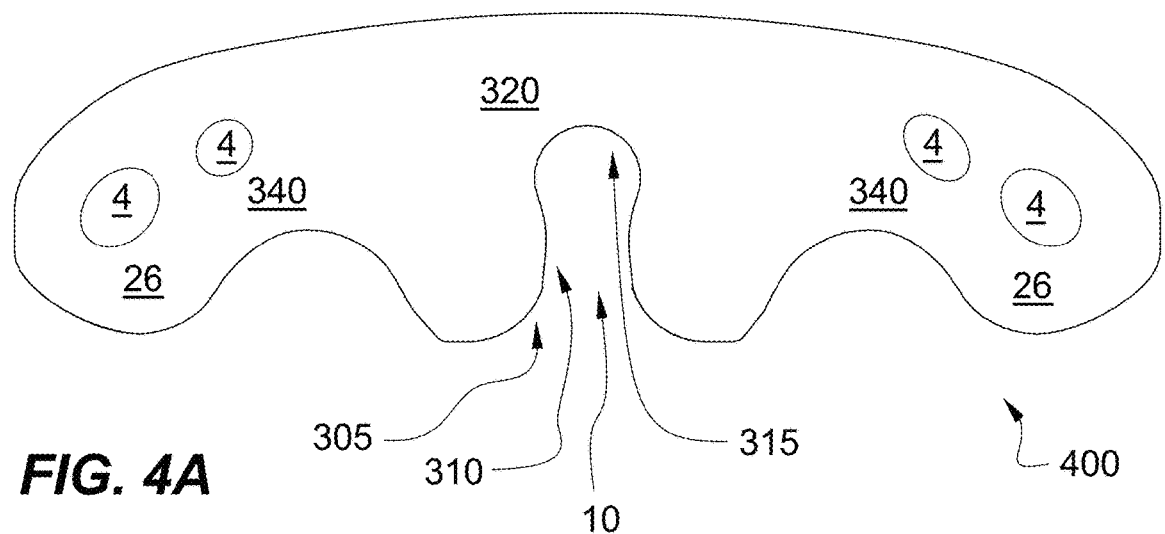
FIGS. 4A and 4B, collectively
Figure 4B:
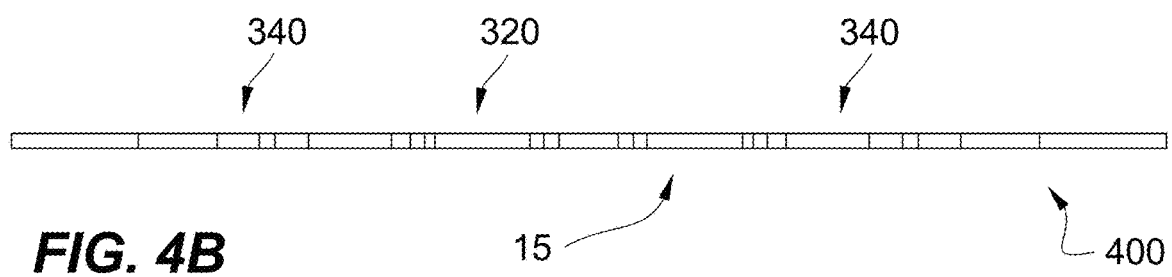

Turning now to FIGS. 4A and 4B, these figures illustrate an example blank 400 to be formed into an example ring 300 for fastening a plunger 21 to a user 5 according to some embodiments of the disclosure. (See FIGS. 1 and 2, among other places, for example ring, plunger, and user illustrations.) FIG. 4A illustrates an overhead view (showing a major surface of the blank 400), while FIG. 4B illustrates a side view showing an edge thereof.

FIG. 4 provides reference numbers and lead lines indicating representative portions of the blank 400 corresponding to like-numbered features of the ring 300 illustrated in FIG. 3. When the blank 400 is formed, regions of the flat sheet of material can be transformed into three-dimensional contours of the ring 300 generally following the like numbers of FIGS. 3 and 4.

In some embodiments, the blank 400 comprises a thin sheet of workable metal alloy that is formed using metal working processes that create three-dimensional contours using permanent deformation. Representative metal working processes can include using tools and dies and/or bending over mandrels, among other techniques available to those of skill in the art having benefit of this disclosure. Specific portions can be heated and cooled in a manner that imparts desired softness or hardness to those regions, so that a user 5 may form a soft region for an individualized fit, for example.

In some example embodiments, the blank 400 comprises a sheet of thermoplastic material. Such a sheet can be transformed to provide the contours of the ring 300 of FIG. 3. For example, the sheet can be heated to soften the material and then formed using a tool and die or a mold or other appropriate process for working thermoplastics.

Figures 5, 6A, 6B:
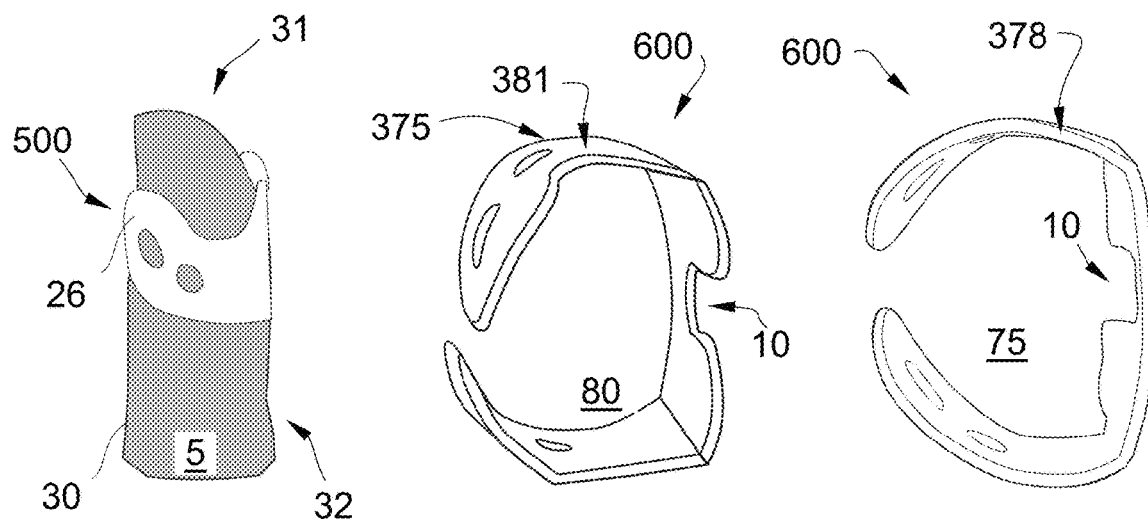
FIG. 5, is an illustration of a ring for fastening a plunger to a user, illustrated disposed on thumb, in accordance with some example embodiments of the disclosure.
FIGS. 6A and 6B, collectively

Turning now to FIG. 5, this figure illustrates an example ring 500 for fastening a plunger 21 to a user 5, depicted in the example configuration of disposed on a thumb 30 according to some embodiments of the disclosure. (See FIGS. 1 and 2 for example plunger illustrations.) The ring 500 can be utilized for fastening in accordance with the illustrations and associated discussion of FIGS. 1 and 2 and further with other teaching provided herein.

In some example embodiments, the ring 500 has a composition of a material that is sufficiently malleable so the user 5 can form the ring 500 by hand for an individualized fit to the user's thumb 30. As an example of forming the ring 500 by hand for an individualized fit, the user 5 may hold the ring 500 in the user's nondominant hand while bending the ring ends 26 with the user's dominant hand, without aid of a tool. In the context of describing malleability for forming by hand, such a user 5 may be a healthy male U.S. resident who is 35-45 years of age; is of average stature, body type, and weight; and has average strength. Of course, a wide range of users 5 of various ages, nationalities, residencies, genders, strengths, demographics, etc. may form various ring embodiments by hand.

In some example embodiments, the ring 500 has a metallic composition and may comprise one or more metals or metal alloys, may substantially consist of one or more metals or metal alloys, or may consist of one or more metals or metal alloys. In some embodiments, the ring 500 can comprise (or can consist or substantially consist of) a unitary piece of malleable metal, and the metal may comprise an alloy.

In some example embodiments, the ring 500 comprises a metal alloy and is supplied to the user 5 with the metal alloy annealed. In some example embodiments, as supplied to the user, a portion of the ring 500 is annealed. In some example embodiments, one or more selected portions of the ring 500 may be annealed to facilitate user forming of those ring portions. For example, the ring ends 26 may be annealed while the floor 320 of the ring 500 may be work hardened or otherwise hard relative to the annealed portion.

In some example embodiments, the material of the ring 500 can have a tensile strength, a yield strength, an elongation, or a hardness that has a numerical value that is within 25 percent of the corresponding numerical value of sterling silver. In some example embodiments, the material of the ring 500 can have a tensile strength, a yield strength, an elongation, or a hardness that has a numerical value that is within 10 percent of the corresponding numerical value of sterling silver. In some example embodiments, the material of the ring 500 can have a tensile strength, a yield strength, an elongation, or a hardness that is no greater than that of sterling silver. Some example embodiments may substantial deviate from the example values disclosed in this paragraph.

In some example embodiments, the ring 500 can have a material property, as annealed, that is in a range between 70 percent and 140 percent of any of the following values: tensile strength—207 MPa; yield strength—124 MPa; elongation—41%; tensile strength (wire)—283 MPa; elongation (wire)—40%; or hardness (wire)—71 HV. In some example embodiments, the ring 500 can have a material property, as half-hard, that is in a range between 70 percent and 140 percent of any of the following values: tensile strength (wire)—386 MPa; and hardness (wire)—95 HV. In some example embodiments, the ring 500 can have a material property, as full hard, that is in a range between 70 percent and 140 percent of any of the following values: tensile strength (wire)—496 MPa; and hardness (wire)—123 HV. In some example embodiments, the ring 500 can have a material property, as spring hard, that is in a range between 70 percent and 140 percent of any of the following values: tensile strength (wire) 552—MPa; and hardness (wire)—140 HV. The material properties disclosed in this paragraph (as with other materials and material properties disclosed at other portions of the detailed description) are examples; various embodiments may substantially deviate from these materials and properties, as may be deemed desirable for various applications and preferences.

FIG. 5 illustrates the ring 500 worn at an example location of a user's thumb 30. Various users 5 may have thumbs 30 of different sizes and shapes or may wear the ring at different locations on their thumbs 30 or on a finger other than a thumb 30 or on another appendage. A capability for user customization can help accommodate different user physiques, different user preferences, different plunger flanges 22, and different applications, for example.

In some example embodiments, the ring 500 is supplied to the user 5 with one or more mandrels, pliers, or other appropriate tools. The user 5 may utilize such tools to form the ring 500 to achieve a custom shape or personalized fit. In such embodiments, customization can be realized even if the user 5 cannot form the ring 500 barehandedly, for example when the ring 500 is too strong and/or the user 5 is not strong enough.

In some example embodiments, the user 5 may wear the ring 500 on a distal portion 31 the thumb 30, perhaps covering the fingernail (not shown in FIG. 5) where the thumb 30 is curved. The ring 500 may be formed (by the user 5 or by its manufacturer) with a corresponding curve in some example embodiments. In some example embodiments, the user 5 may wear the ring 500 over the interphalangeal joint 91 of the thumb 30, and the user 5 or the manufacturer may form the ring 500 to fit that anatomy. See FIG. 1D for an example illustration of the interphalangeal joint 91 disposed in the ring 500.

In some example embodiments, the user 5 may wear the ring 500 on a finger other than the thumb 30, or may wear the ring 500 on another appendage. The user 5 or the manufacturer may form the ring 500 to fit another finger or appendage, for example.

Turning now to FIGS. 6A and 6B, these figures illustrate an example ring 600 for fastening a plunger 21 to a user 5 according to some embodiments of the disclosure. (See FIG. 1 for example plunger and user illustrations.) The ring 600 can be utilized for fastening in accordance with the illustrations and associated discussion of FIGS. 1 and 2 and further with other teaching provided herein.

In the illustrated embodiment of FIG. 6, the proximal opening 75 of the ring 600 is larger than the distal opening 80 of the ring 600. As illustrated, the ring 600 tapers up longitudinally, between the distal edge 381 of the ring 600 and the proximal edge 378 of the ring 600. In the illustrated example embodiment, the slot 10 starts at the distal edge 381 of the ring 600 and extends towards the proximal edge 378. In some other example embodiments, the slot 10 starts at the proximal edge 378 of the ring 600 and extends towards the distal edge 381.

Figure 7:
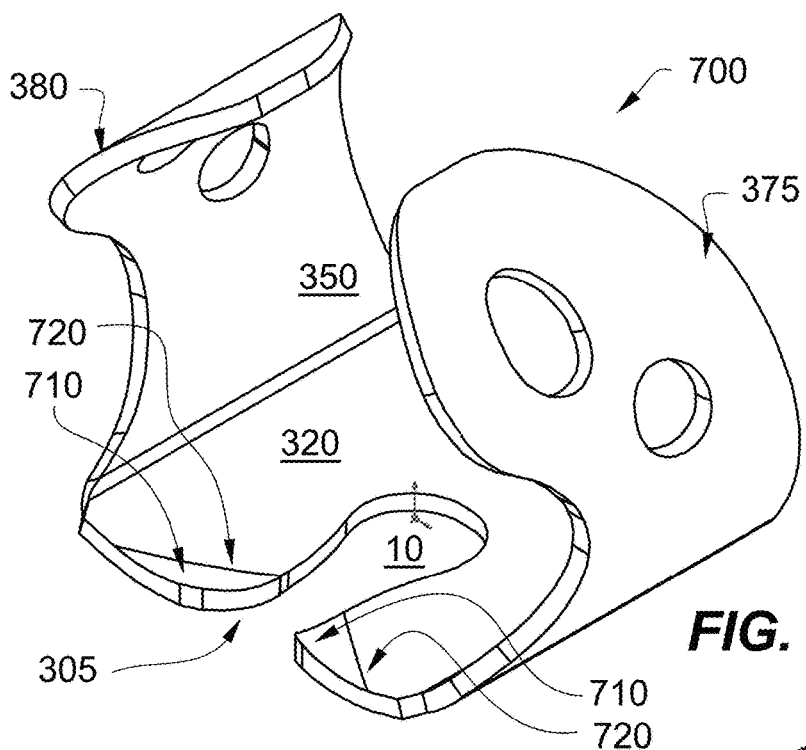
FIG. 7 is an illustration of a ring for fastening a plunger to a user in accordance with some example embodiments of the disclosure.

Turning now to FIG. 7, this figure illustrates an example ring 700 for fastening a plunger 21 to a user 5 according to some embodiments of the disclosure. (See FIG. 1 for example plunger and user illustrations.) The ring 1000 can be utilized for fastening in accordance with the illustrations and associated discussion of FIGS. 1 and 2 and further with other teaching provided herein.

In the example embodiment of FIG. 7, the floor 320 of the ring 700 is formed to promote retention and seating of the flange 5. As illustrated, the mouth 305 of the slot 10 in the floor 320 projects upward. More specifically two areas 710 that form the mouth 305 of the slot are bent into the interior space 350 of the ring 700. As illustrated, the bends largely occur at a crease line 720. These bends can be formed by positioning a corner or edge of a tool at the desired position and forming over the edge, resulting in the crease line 720. The bends can be more arching or more gradual based on the profile of the tool edge or by forming over a rod or other rounded surface. To facilitate such forming, the ring 700 can have a composition of malleable metal, for example annealed metal, gold, sterling silver, Argentium silver, copper, or other appropriate metal or metal alloy. In some embodiments, the ring 600 comprises stainless steel. In some examples, the illustrated contours and features are formed by injection molding a thermoplastic material.

FIG. 7 illustrates the ring 700 with the slot mouth 305 at the distal portion of the ring 700. In some other example embodiments, the slot mouth 305 is at the proximal portion of the ring 700.

Figure 8A:
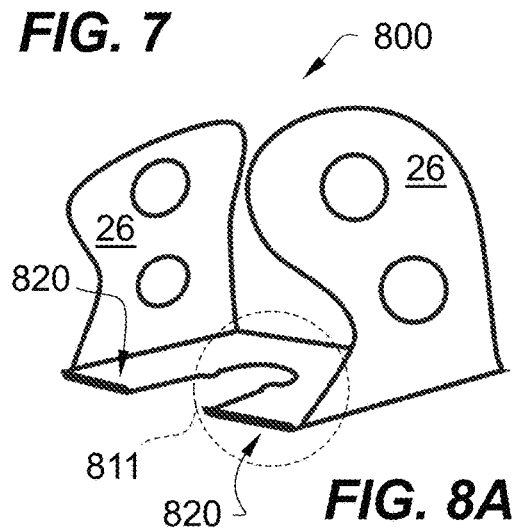
FIGS. 8A and 8B, collectively
Figure 8B:
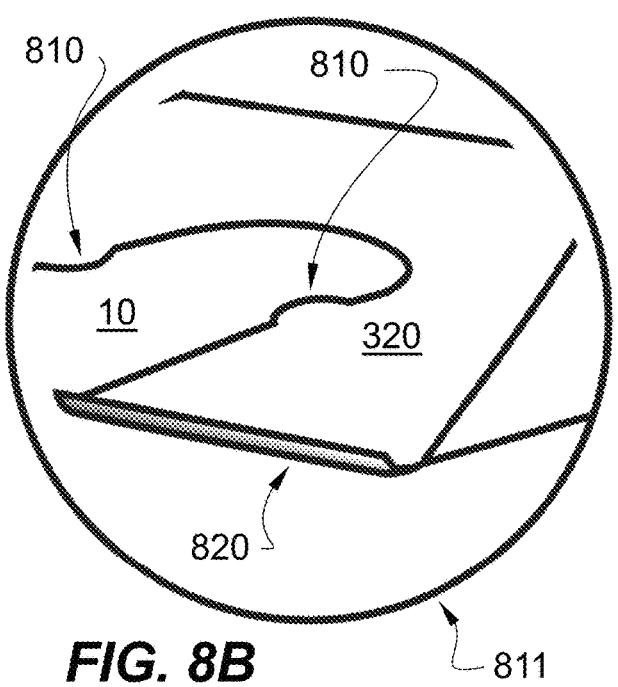

Turning now to FIGS. 8A and 8B, these figures illustrate an example ring 800 for fastening a plunger 21 to a user 5 according to some embodiments of the disclosure. (See FIG. 1 for example plunger and user illustrations.) FIG. 8B provides a magnified view of a portion 811 of the ring 800 that is outlined in FIG. 8A. The ring 800 can be utilized for fastening in accordance with the illustrations and associated discussion of FIGS. 1 and 2 and further with other teaching provided herein.

As best seen in the magnified view of FIG. 8B, the ring 800 comprises a distally oriented curled edge 820 adjacent the slot 10. The curled edge 820 can help secure the plunger flange 20 against the floor 320. The slot 10 comprises a pair of nubs 810 that promote retention of the plunger shaft 23 in the slot 10.

In the example ring 800, the ends 26 are oriented upright relative to the floor 320. In some embodiments, the ring 800 is supplied in this configuration in malleable metal, and the user 5 bends the ring 800 as desired for a custom fit.

Figure 9:
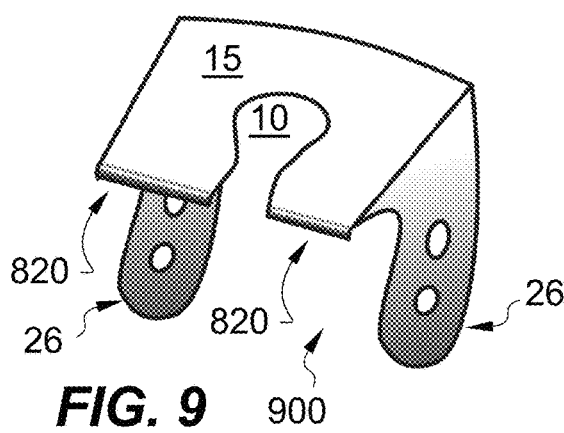
FIG. 9 is an illustration of a ring for fastening a plunger to a user in accordance with some example embodiments of the disclosure.

Turning now to FIG. 9, this figure illustrates an example ring 900 for fastening a plunger 21 to a user 5 according to some embodiments of the disclosure. As illustrated, the ring 900 is positioned to show the lower exterior surface 15, including a curled edge 820 that is similar in form and function to the curled edge 820 illustrated in FIG. 8 and discussed above. The slot 10 in the ring 900 is rounded and wide at its closed end relative to the slot 10 of the ring 800 of FIG. 8.

Turning now to FIGS. 10A and 10B, these figures illustrate an example ring 1000 for fastening a plunger 21 to a user 5 according to some embodiments of the disclosure. (See FIG. 1 for example plunger and user illustrations.) The ring 1000 can be utilized for fastening in accordance with the illustrations and associated discussion of FIGS. 1 and 2 and further with other teaching provided herein. FIG. 10A illustrates the ring 1000 with the distal opening 80 and the distal portions of the ring 1000 facing out of the page. Meanwhile, FIG. 10B illustrates the ring 1000 with those features oriented left and the proximal portions of the ring 1000 oriented right.

As best seen in FIG. 10B, the floor 320 of the ring 1000, and thus the lower exterior surface 15 of the ring 1000, bulges downward. This provides a recessed space 370 that is inside the ring 1000 associated with the slot 10 for receiving flanges 22 of different geometries that different manufacturers produce.

Turning now to FIG. 11, this figure illustrates a portion of an example ring 1100 for fastening a plunger 21 to a user 5 (not depicted in FIG. 11) according to some embodiments of the disclosure. More specifically, FIG. 11 illustrates a cross section of the ring 1100 and the plunger 21, with the plunger's shaft 23 extending through the slot 10 in the floor 320 of the ring 1100.

In the example embodiment of FIG. 11, the floor 320 comprises a recessed area 1170 in which the flange 22 of the plunger 21 is disposed and is seated. As illustrated, the recessed area 1170 is sized to receive the flange 22. In some example embodiments, the recessed area 1170 is configured to receive a wide range of flange sizes and geometries as produced from different manufacturers. In some other example embodiments, the recessed area 1170 has a geometry designed for selective compatibility with a particular manufacturer's flanges. For example, the shape and/or dimensions of the recessed area 1170 may receive proprietary flanges of one manufacturer that have a corresponding size and/or dimensions (or other matching physical features) without fully accommodating other flanges from other manufacturers.

Figure 12:
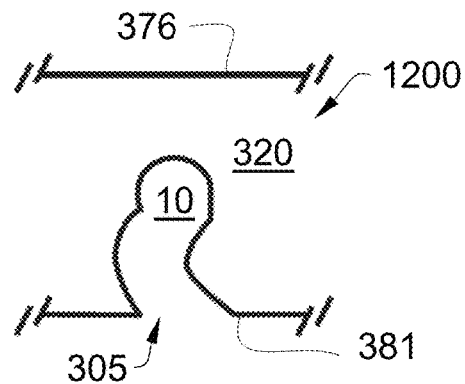
FIG. 12 is an illustration of a portion of a ring for fastening a plunger to a user in accordance with some example embodiments of the disclosure.

Turning now to FIG. 12, this figure illustrates a portion of an example ring 1200 for fastening a plunger 21 to a user 5 according to some embodiments of the disclosure. (See FIG. 1 for example plunger and user illustrations.) FIG. 12 illustrates a floor 320 of the ring 1200 with an example slot 10 that is curved along its length. The illustrated portion of the ring 1200 can be utilized for fastening in accordance with the illustrations and associated discussion of FIGS. 1 and 2 and further with other teaching provided herein.

As illustrated at FIG. 12, the slot 10 has a mouth 305 at the distal edge 381 and extends from the distal edge 381 towards the proximal edge 376. In some other embodiments, the mouth 305 is at the proximal edge 376, and the slot 10 extends from the mouth 305 towards the distal edge 381. In various embodiments, the floor 320 can have a metallic or plastic composition, and/or comprise multiple components of different materials joined together.

In this illustrated example, the slot 10 deviates from linear along a path from the mouth at distal edge 381 towards proximal edge 376. The deviation from linear can help secure or retain the plunger 21 in the slot 10, for example. In various embodiments, the path of the slot 10 may be sinusoidal, sinuous, serpentine, arced, bent, or another appropriate form of a curve. In some example embodiments, the path is of the slot 10 includes one or more corners, a sharp bend, or may turn back on itself. For example, the path may have shape of the letter "J." In such an embodiment, the top of the "J" may be at the distal edge 381 and the curved bottom of the letter "J" may be oriented towards the proximal edge 376. In various example embodiments, the slot 10 follows another appropriate path operable to fasten the plunger 21 to the user 5.

Figure 13:
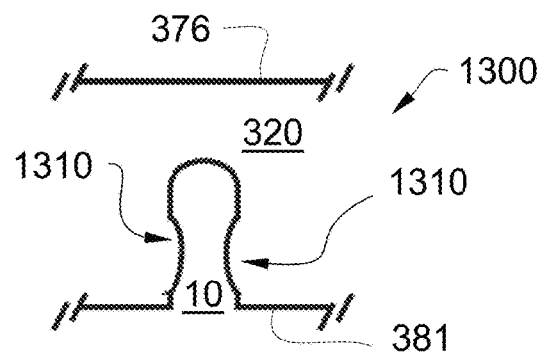
FIG. 13 is an illustration of a portion of a ring for fastening a plunger to a user in accordance with some example embodiments of the disclosure.

Turning now to FIG. 13, this figure illustrates a portion of an example ring 1300 for fastening a plunger 21 to a user 5 according to some embodiments of the disclosure. (See FIG. 1 for example plunger and user illustrations.) FIG. 13 corresponds to FIG. 12, as discussed above. The illustration portion of the ring 1300 can be utilized for fastening in accordance with the illustrations and associated discussion of FIGS. 1 and 2 and further with other teaching provided herein.

As illustrated by FIG. 13, the slot 10 starts at the distal edge 381 and extends from the distal edge 381 towards the proximal edge 376. In some other embodiments, the slot 10 is open at the proximal edge 376 and extends towards the distal edge 381.

In the example embodiment of FIG. 13, the slot 10 has sidewall regions 1310 that bow inward to help secure or retain the plunger 21 in the slot 10. In some embodiments, the bow sufficiently narrows the slot 10 so that interference exists between the outer diameter of the plunger shaft 23 and the slot 10. Thus, at least some material deformation can occur upon insertion of the plunger 21 into the slot 10, thereby aiding plunger retention.

Figure 14:
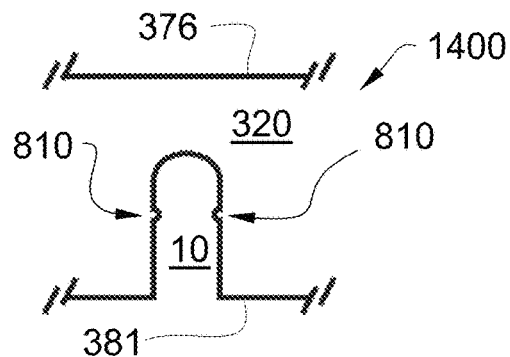
FIG. 14 is an illustration of a portion of a ring for fastening a plunger to a user in accordance with some example embodiments of the disclosure.

Turning now to FIG. 14, this figure illustrates a portion of an example ring 1400 for fastening a plunger 21 to a user 5 according to some embodiments of the disclosure. (See FIG. 1 for example plunger and user illustrations.) FIG. 14 corresponds to FIGS. 12 and 13, as discussed above. The illustration portion of the ring 1400 can be utilized for fastening in accordance with the illustrations and associated discussion of FIGS. 1 and 2 and further with other teaching provided herein.

As illustrated in FIG. 14, the slot 10 starts at the distal edge 381 and extends from the distal edge 381 towards the proximal edge 376. In some other embodiments, the slot 10 is open at the proximal edge 376 and extends towards the distal edge 381.

In the example embodiment of FIG. 14, the slot 10 has nubs 810 that narrow the slot 10 to help secure or retain the plunger 21 in the slot 10. In some example embodiments, the nubs 810 can comprise sharp or pointed perturbances. In some example embodiments, the nubs 810 are formed of different material than the rest of the floor 320. For example, the floor 320 can be formed of plastic material and nubs made of metal inserted into the plastic material during injection molding or other appropriate fabricating operation. The illustrated example embodiment of FIG. 14 can comprise a composite structure or a can be formed of homogenous material.

Figure 15:
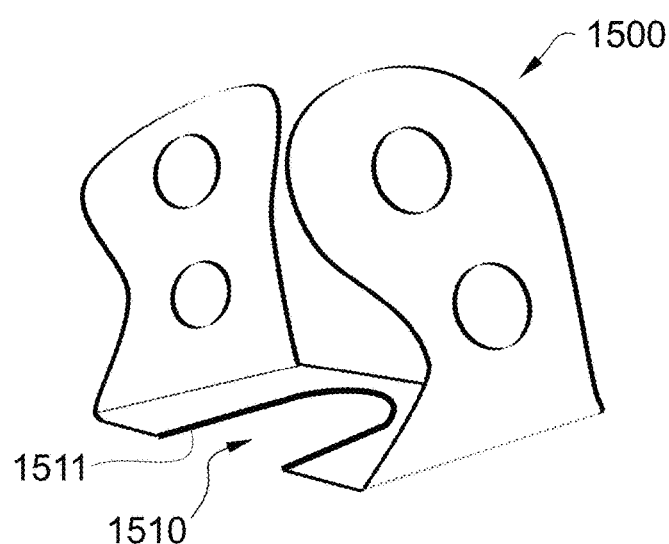
FIG. 15 is an illustration of a ring for fastening a plunger to a user in accordance with some example embodiments of the disclosure.
Figure 16:
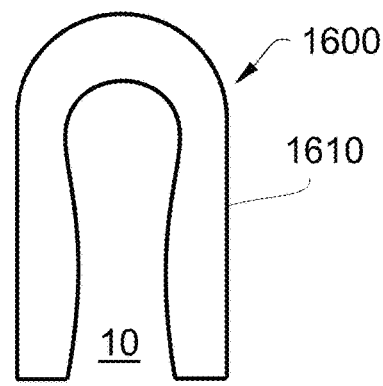
FIG. 16 is an illustration of a portion of a ring for fastening a plunger to a user in accordance with some example embodiments of the disclosure.
Figure 17:
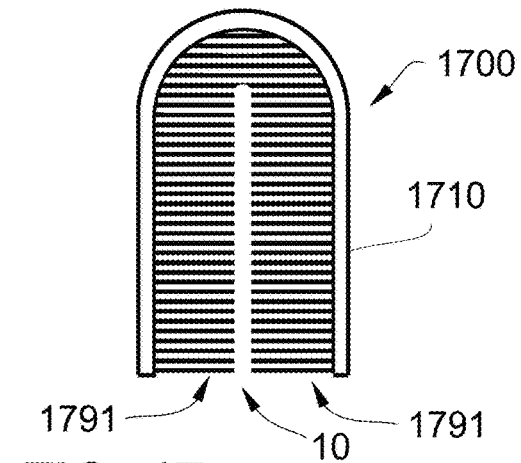
FIG. 17 is an illustration of a portion of a ring for fastening a plunger to a user in accordance with some example embodiments of the disclosure.

Turning now to FIGS. 15, 16, and 17, these figures will be discussed. FIG. 15 illustrates an example ring 1500 for fastening a plunger 21 to a user 5 according to some embodiments of the disclosure. FIGS. 16 and 17 illustrate respective portions of an example ring 1500 for fastening a plunger 21 to a user 5 according to some embodiments of the disclosure. (See FIG. 1 for example plunger and user illustrations.) As further discussed below, FIGS. 16 and 17 respectively illustrate inserts 1600, 1700 that mate with receptacle 1510 of the ring 1500 illustrated in FIG. 15. In combination with one of the inserts 1600, 1700, the ring 1500 can be utilized for fastening in accordance with the illustrations and associated discussion of FIGS. 1 and 2 and further with other teaching provided herein.

The insert 1600 illustrated in FIG. 16 is sized for insertion in and reception by the receptacle 1510 of the ring 1500, to become a component of the ring 1500. The insert 1600 comprises a slot 10 that may be configured in accordance with the various slot embodiments disclosed herein.

In some example embodiments, the insert 1600 is configured for compatibility with a particular type or brand of syringe 27. In some example embodiments, the insert 1600 can be optimized for a specific manufacturer's syringes or may be configured to work only with a proprietary plunger. A syringe manufacturer may supply the insert 1600 so the user 5 can change out the insert 1600 as needed, for example on a procedure-by-procedure basis or otherwise as desired.

In some example embodiments, the insert 1600 can be snapped into the receptacle 1510 by the user 5, for example. In some embodiments, the ring 1500 is formed of a material that is harder than the insert 1600 to facilitate user assembly. For example, the insert 1600 can be made of plastic or synthetic rubber, and the ring 1500 can be made of metal. As another example, the ring 1500 and the insert 1600 can both be made of plastic materials having different durometers, with the ring 1500 having a higher durometer than the insert or vice versa.

In some embodiments, the insert 1600 can comprise a groove (not illustrated) that extends about the outer periphery 1610 of the insert 1600. Such a groove can receive the edges 1511 of the ring 1500 that form the receptacle 1510. Thus, the insert 160 can snap into the receptacle 1510 in a tongue-in-groove configuration, with the insert 1600 comprising the groove and the receptacle edge 1511 comprising the tongue.

As illustrated, the receptacle 1510 comprises a slot with substantially parallel sides. In some embodiments, the edges 1511 of the receptacle 1510 can be curved to promote retention of the insert 1600. For example, the receptacle 1510 can have a width that increases with depth, and the insert 1600 can have a corresponding geometry.

In some example embodiments, the insert 1600 is permanently joined with the receptacle 1510 during manufacture of the ring 1500. For example, the insert 1600 can be fused, epoxied, welded, bonded, or otherwise attached to the ring 1500.

The receptacle 1510 of the ring 1500 can receive the insert 1700 illustrated in FIG. 17 in keeping with the foregoing discussion of the insert 1600. In some example embodiments, the insert 1700 comprises a pliable material 1791 that extends inward from the outer periphery of the insert 1700. The pliable material 1791 can comprise a thin sheet of elastomeric material, such as silicone or synthetic rubber, with the slot 10 formed in the sheet, for example.

In some embodiments, the pliable material 1791 comprises thin filaments, for example bristles, whiskers, or fibers, that extend inward from the periphery 1710 of the insert 1700 towards the slot 10. The slot 10 can thus be formed by the ends of such filaments, which can comprise natural or synthetic fibers, for example as may be incorporated in a typical hairbrush.

Figure 22:
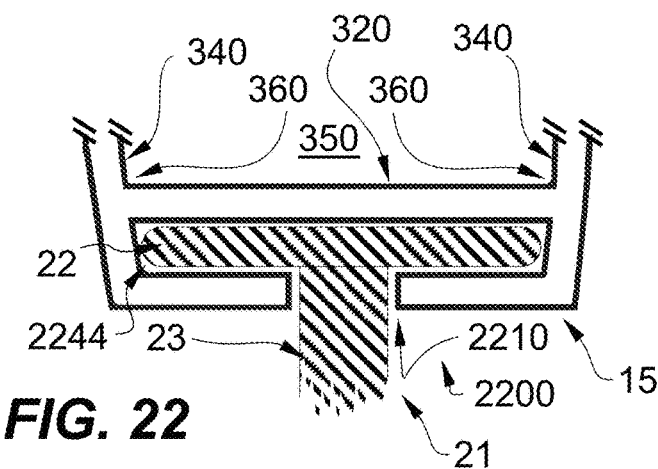
FIG. 22 is an illustration of a portion of a ring for fastening a plunger to a user in accordance with some example embodiments of the disclosure.

In some embodiments, such filaments are attached directly to the ring 1500, without use of an insert. In some embodiments, such filaments form an aperture other than a slot, for example a circle, rectangle, or other closed geometric form in a floor 320 of a ring. FIG. 22, as further discussed below, illustrates an example embodiment of a geometric form.

Turning now to FIGS. 18A and 18B, these figures illustrate an example ring 1800 for fastening a plunger 21 to a user 5 according to some embodiments of the disclosure. (See FIG. 1 for example plunger and user illustrations.) The ring 1800 can be utilized for fastening in accordance with the illustrations and associated discussion of FIGS. 1 and 2 and further with other teaching provided herein.

The example ring 1800 illustrated in these FIGS. 18A and 18B comprises flexible material and straps on with a catch 1864 that can provide a snug or secure fit. In the illustrated embodiment, the ring 1800 can be characterized as comprising a strap that can be tightened.

As illustrated by FIG. 18A, the ends 26A, 26B of the ring 1800 are depicted in a free state. In the illustration of FIG. 18B, the catch 1864 has the ends 26A, 26B connected to one another.

In the illustrated example, the catch 1864 comprises an array of protrusions 1866 disposed on the end 26B and an aperture 1844 in the end 26A. The aperture 1844 is sized to receive the end 26B. As illustrated, the protrusions 1866 are curved to engage the periphery of the aperture 1844 once the end 26B is sufficiently inserted in the aperture 1844. In some other example embodiments, the catch 1864 can comprise a buckle, clasp, clamp, clip, hasp, or other appropriate device.

FIG. 18B illustrates the ring 1800 as may be disposed on a user's thumb 30 prior to tightening. Once on the thumb 30 in the configuration illustrated in FIG. 18B, the user 5 can tighten the ring 1800 by pulling on the free end 26B, for example upward or in a direction so the end 26B turns somewhat back on its self. The slot 10 provides for fastening the plunger 21 to the user 5 as discussed above with reference to FIGS. 1 and 2.

In some example embodiments, the ring 1800 can comprise a flexible synthetic material or a combination of such materials, such as nylon, acetal resin, silicone, vinyl, flashspun high-density polyethylene fibers, one or more elastomers, or other appropriate material. In some example embodiments, the ring 1800 can comprise nonwoven fabric.

In some example embodiments, the ring 1800 comprises a homogenous thermoplastic, for example nylon. In some embodiments, the floor 320 is thick relative to the end 26A and the end 26B. Thickening the floor 320 can enhance stiffness of this area of the ring 1800.

In the illustrated embodiment, the ring 1800 comprises corners 360 adjacent the floor 320. The corners 360 can result from manufacturing the ring 1800 with pre-defined corners, so the corners 360 exist with the ring 1800 is in a relaxed state or prior to strapping on the ring 1800. For example, the ring 1800 can be injection molded from thermoplastic material in a mold having a corresponding corner. As another alternative, the corners 360 may be formed in a flat strip of thermoplastic by heating the strip at a location where the corner 360 is desired to soften the material, bending the strip at that location, and then cooling the material.

Turning now to FIG. 19, this figure illustrates an example ring 1900 for fastening a plunger 21 to a user 5 according to some embodiments of the disclosure. (See FIG. 1 for example plunger and user illustrations.) The ring 1900 can be utilized for fastening in accordance with the illustrations and associated discussion of FIGS. 1 and 2 and further with other teaching provided herein.

Similar to the embodiment illustrated in FIG. 18 and discussed above, the example ring 1900 is configured for strapping to a thumb 30 of the user 5 by inserting the end 26B in the aperture 1844 of the end 26A and tightening.

In the example embodiment illustrated in FIG. 19, the aperture 1944 comprises a slit that may formed be formed in the end 26A by cutting without material removal. Relative to the embodiment illustrated by FIG. 18, the protrusions 1966 on the end 26B are smaller and more numerous, which may support a fine level of control of tightening as may be appropriate in some environments or applications.

For the embodiment of FIG. 19, the ring 1900 can be formed from a thin strip of material. In some examples, the material comprises a thermoplastic such discussed above with reference to the ring 1800 illustrated by FIG. 18. To facilitate formation of corners 360 (see FIG. 18) adjacent the floor 320 when worn by the user 5, features 1960 can be formed in strip of material. For example, the features can be formed in the strip with scribing, perforations, notching, deformations, thinning, stress deformation, heating, creasing, or other appropriate means.

Turning now to FIG. 20, this figure illustrates an example portion of a ring 200 for fastening a plunger 21 to a user 5 according to some embodiments of the disclosure. (See FIG. 1 for example plunger and user illustrations.) The illustrated portion of the ring 2000 can be utilized for fastening in accordance with the illustrations and associated discussion of FIGS. 1 and 2 and further with other teaching provided herein.

FIG. 20 illustrates a floor 320 of the ring 2000 and portions of the interior surface 340 of the ring 2000. In the illustrated example of FIG. 20, the ring 2000 comprises features 1960 associated with a corner, crease, or sharp bend, for example as discussed above with reference to FIG. 19.

An aperture 2010 is formed in or disposed adjacent the floor 320 and is disposed between a distal portion 380 and a proximal portion 375 of the ring 2000. The aperture 2010 is configured for receiving and securing a flange 22 of a plunger 21. As illustrated, the example aperture 2010 comprises two slit areas 2001 that oppose one another, each extending towards a respective one of the features 1960. The illustrated aperture 2010 comprises one example embodiment of a slot.

In an example embodiment, the floor 320 comprises an elastomeric sheet of material, and the aperture 2010 is formed in that material. In operation, the user 5 can use the slit areas 2001 of the aperture 2010 to work the flange 22 into the aperture 2010. The distance between the opposing ends of the slit areas 2001 can correspond to the width of the flange 22, so that the aperture 2010 can receive the flange 22. For example, the distance between the opposing ends of the slit area 2001 can be less than the width of the flange 22, so that the user may stretch the elastomeric material to open the aperture 2010 for insertion of the flange 22.

In some example embodiments, the flange 22 is rectangular, oblong, or oval. In some such embodiments, the user may use the narrow dimension of the flange 22 to work the flange 22 into the aperture 2010. Once in, the user 22 may rotate the flange 90 degrees so the flange 20 is held securely behind the floor 320.

In some example embodiments, the user's thumb 30 (or a medical glove) directly contacts at least a portion of the elastomeric sheet of the floor 320. In such embodiments, the flange 22 may likewise contact the user's thumb 30 when the flange 22 is inserted in the aperture and the ring 2000 is on the user's thumb 30. Alternatively, a portion of the ring 2000 may be disposed between the user's thumb 30 and the flange 22. For example, the ring 1900 illustrated in FIG. 19 or the ring 300 illustrated in FIG. 3 can be formed without the illustrated slot 10, so the floor 320 of the ring 1900 or the ring 300 is unbroken. An elastomeric sheet comprising the aperture 2010 can be attached to the ring 1900 or the ring 300 so that the sheet forms a lower exterior surface of the ring 1900 or 300 (in the location indicated by reference number 15 on FIG. 3).

Turning now to FIG. 21, this figure illustrates an example portion of a ring for fastening a plunger 21 to a user 5 according to some embodiments of the disclosure. (See FIG. 1 for example plunger and user illustrations.) The illustrated portion of the ring 2100 can be utilized for fastening in accordance with the illustrations and associated discussion of FIGS. 1 and 2 and further with other teaching provided herein. In some example embodiments, features of the ring 2100 illustrated in FIG. 21 can be implemented and practiced in keeping with the foregoing discussion of FIG. 20.

As illustrated, the aperture 2110 of the ring 2100 comprises a single slit area 2101 that is oriented towards the distal portion 380 of the ring 2100, generally parallel to the features 1960. In some other example embodiments, the slit area 2101 is oriented towards the proximal portion 375 of the ring 2100. In some example embodiments, the slit area 2101 is oriented towards either of the features 1960 or at an angle in between them.

Turning now to FIG. 22, this figure illustrates an example portion of a ring 2200 for fastening a plunger 21 to a user 5 according to some embodiments of the disclosure. (See FIG. 1 for an example user illustration.) The illustrated portion of the ring 2200 can be utilized for fastening in accordance with the illustrations and associated discussion of FIGS. 1 and 2 and further with other teaching provided herein.

FIG. 22 illustrates an example embodiment in which a floor 320 of the ring 2200 separates the flange 22 from the user's thumb 30, which is a configuration discussed above with reference to FIG. 20. The ring 2200 comprises a cavity 2244, in which the flange 22 is disposed, and a slot 2210 through which the shaft 23 extends. A lower exterior surface 15 of the ring 2200 extends below the cavity 2244. The ring 2200 further comprises corners 360 and interior surfaces 340 that extend about an interior space 350 in which the user's thumb 30 is disposed when the ring 2200 is worn.

Figure 23B:
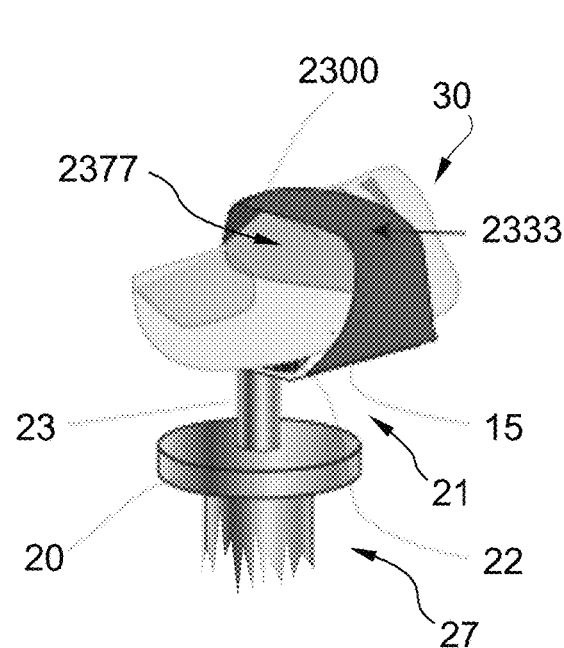
FIGS. 23A and 23B, collectively
Figure 23A:
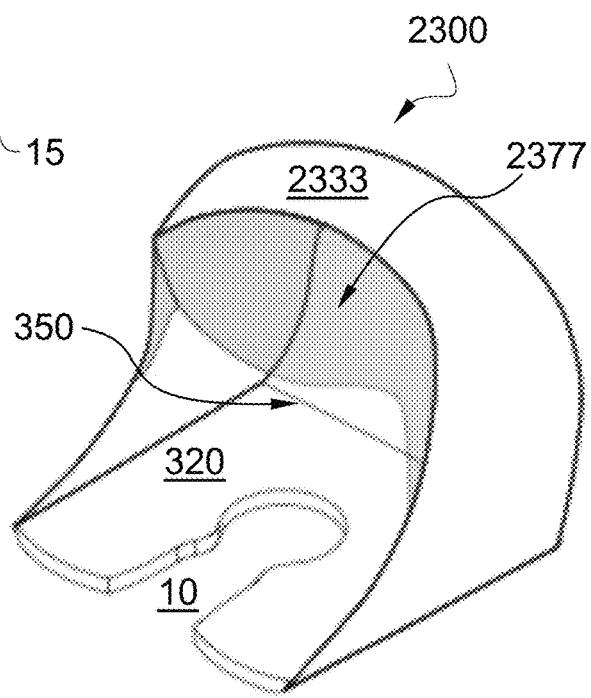
Figure 24:
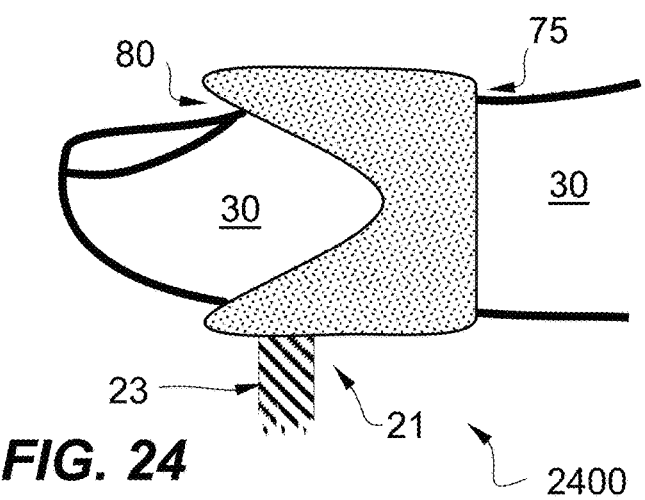
FIG. 24 is an illustration of a ring for fastening a plunger to a user in accordance with some example embodiments of the disclosure.

Turning now to FIGS. 23A and 23B, these figures illustrate an example ring 2300 for fastening a plunger 21 to a user 5 according to some embodiments of the disclosure. As illustrated in FIG. 23B, the example ring 2300 extends continuously and fully around the user's thumb 30 when worn. A plastic material 2377 extends across an upper region of the interior space 350 of the ring 2300 and is attached to the upper portion 2333 of the ring 2300. The plastic material 2377 extends from the upper portion 2333 of the ring 2300 towards the floor 320, the slot 10, and the lower exterior surface 15 of the ring 2300. In operation, as shown in FIG. 23B, the plastic material 2377 deforms and presses on the thumb 30 to ensure a snug fit. In some example embodiments, the plastic material 2300 comprises a thin sheet of thermoplastic or silicone. In some example embodiments, the plastic material 2300 comprises a bladder or balloon. In some example embodiments, the entire ring 2300 can have a plastic composition that comprises one or more appropriate materials disclosed herein or otherwise available in the art.

Turning now to FIG. 24, this figure illustrates an example ring 2400 for fastening a plunger 21 to a user 5 according to some embodiments of the disclosure. In the illustrated example embodiment, the ring 2400 fully circumscribes the thumb 30 on which the ring 2400 is worn.

As illustrated, the ring 2400 comprises a slot (hidden in the view of FIG. 24) in accordance with the slot 10 illustrated in FIG. 23A or another appropriate slot supported by the present disclosure. The ring 2400 fastens the plunger 21 to the thumb 30 of the user 5, with the shaft 23 of the plunger 21 protruding through the slot 10, and with the flange 22 (hidden in the view of FIG. 24) disposed between the ring 2400 and the thumb 30.

The thumb 30 extends from the proximal aperture 75 of the ring 2400 to the distal opening 80 and protrudes out of the distal opening 80. As illustrated, the interphalangeal joint 91 of the thumb 30 (illustrated at FIG. 1D) is disposed inside the ring 2400 and is hidden in the present view. In operation, a user 5 can flex this joint 91 during retraction of the plunger 21. Flexing the interphalangeal joint 91 can press the lower surface 71 of the thumb 30 against the flange 22 while pressing the upper surface of the interphalangeal joint 91 against the upper interior surface of the ring 2400. Thus, gap is taken up and pressure is maintained against the flange 22 during retraction of the plunger 21. In some embodiments, hyperextension of the joint 91 can take up gap and similarly provide ongoing force against the plunger flange 22 during plunger retraction.

In some example embodiments, the ring 2400 is formed of a thermoplastic material such as nylon or acetal resin. In some example embodiments, the ring 2400 may be formed of metal or other appropriate material supported by the present disclosure.

Figure 25:
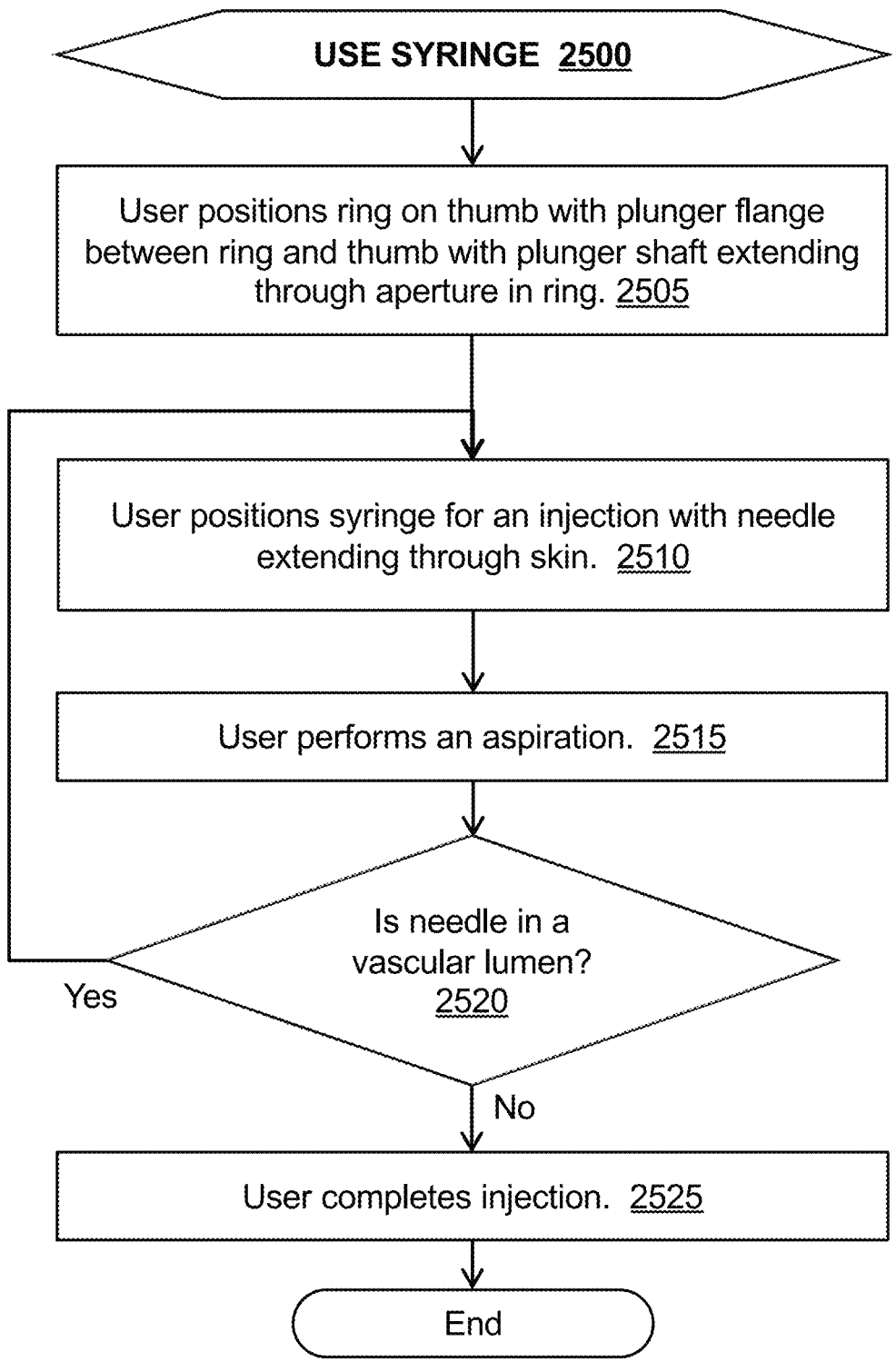
FIG. 25 is a representative flowchart for a process for using a ring for fastening a plunger to a user in accordance with some example embodiments of the disclosure.

Turning now to FIG. 25, this figure illustrates a flowchart for an example process 2500 for using a ring 100 for fastening a plunger 21 to a user 5 according to some embodiments of the disclosure. The flowchart describes the example of operating a plunger 21 of a syringe 27 during a hypodermic injection, without limitation.

Certain steps in process 2500, as well as in the other processes and methods disclosed or taught herein, may naturally need to precede others to achieve desirable functionality. However, the disclosure is not limited to the order of the steps described if such order or sequence does not adversely alter functionality to the extent of rendering the technology inoperable or nonsensical. That is, it is recognized that some steps may be performed before or after other steps or in parallel with other steps without departing from the scope and spirit of the disclosure.

Referring now to the representative flowchart of FIG. 25, an example process 2500 will be further described with example reference to the embodiment illustrated by FIG. 1. Process 2500 can further be practiced with various other embodiments supported by the present disclosure. Accordingly, it will be appreciated that process 2500 can operate with many embodiments and applications, without limitation. Moreover, one of ordinary skill in the art having benefit of this disclosure will be able to practice many variations of process 2500 as may be appropriate for various applications and embodiments.

At block 2505 of process 2500 the user 5 positions the ring 100 on the user's thumb 30 with the flange 22 of the plunger 21 positioned between the ring 100 and the thumb 30. The shaft 23 of the plunger 21 extends through the slot 10 in the ring 100, the slot 10 being an example embodiment of an aperture.

At block 2510 of process 2500, the user 5 positions the syringe 27 for an injection, with the needle 25 extending through the skin 41 of a patient 50. Skin 41 can comprise the patient's face in some examples.

At block 2515 of process 2500, the user 5 aspirates the syringe 27 by retracting the plunger 21. With the ring 100 fastening the plunger 21 to the user's thumb 30, the user 5 may conduct the aspiration with just one hand operating the syringe 27. The user's other hand can be free to steady the patient 50, for example.

At inquiry block 2520, a determination is made as to whether the distal port 88 of the needle 25 of the syringe 27 is positioned in a vascular lumen based on whether the user 5 observes blood entering the syringe 27 as a result of the aspiration.

If the user 5 does not observe blood, the user 5 proceeds with and completes the injection, and process 2500 ends. Completing the injection can comprise injection of dermal filler in some example embodiments.

If, on the other hand, the user 5 observes blood and determines at block 2520 that the syringe 27 is in a vascular lumen, the user withdraws the needle from the patient without completing an injection. Process 2500 branches to block 2510, and the user 5 repositions the syringe 27 to a new location. Process 2500 iterates until finding a suitable location for the injection, at which time the injection is completed.

Technology useful for moving a plunger with dexterity or precision has been described. From the description, it will be appreciated that an embodiment of the disclosure overcomes limitations of the prior art. Those skilled in the art will appreciate that the technology is not limited to any specifically discussed application or implementation and that the embodiments described herein are illustrative and not restrictive. Furthermore, the particular features, structures, or characteristics that are set forth may be combined in any suitable manner in one or more embodiments based on this disclosure and ordinary skill. Those of ordinary skill having benefit of this disclosure can make, use, and practice a wide range of embodiments via combining the disclosed features and elements in many permutations without undue experimentation. This disclosure not only includes the illustrated and described embodiments, but also provides a rich and detailed roadmap for creating many additional embodiments using the various disclosed technologies, elements, features, and their equivalents. From the description of the example embodiments, equivalents of the elements shown herein will suggest themselves to those skilled in the art, and ways of constructing other embodiments will appear to practitioners of the art. Therefore, the scope of the technology is to be limited only by the appended claims.

What is claimed is:

1. An apparatus for fastening plungers of hypodermic syringes to a thumb of a medical practitioner to aid usage of the hypodermic syringes, the apparatus comprising
 a member that is formed of a sheet of malleable metal, that is configured to be worn on the thumb and to extend at least partially around the thumb when worn on the thumb, and that comprises:
  a distal aperture configured so that a distal portion of the thumb extends out of the distal aperture when the member is worn on the thumb;
  a proximal aperture that is configured so that a proximal portion of the thumb extends out of the proximal aperture when the member is worn on the thumb, that is longitudinally displaced from the distal aperture, and that is larger than the distal aperture, wherein the member tapers longitudinally from the proximal aperture to the distal aperture and is formed to fit anatomy of the thumb between said distal and proximal portions of the thumb so that interior contours of the member follow contours of the thumb to promote a snug fit when the member is worn on the thumb;
  a section extending longitudinally from the distal aperture to the proximal aperture and at least partially circumscribing an interior space in which the thumb is disposed when the member is worn on the thumb, wherein the section comprises a floor that extends longitudinally from the distal aperture to the proximal aperture,
   wherein the floor comprises an interior surface that faces the interior space, and
   wherein the interior surface of the floor has a shape that slopes upward from the proximal aperture to the distal aperture to accommodate said contours of the thumb; and
  a slot that is formed in the floor of the section and that is sized to receive shafts of the plungers and to impede passage of flanges of different sizes and geometries of the plungers, the slot comprising:
   a mouth that is disposed adjacent the distal aperture and that narrows with increasing distance from the distal aperture;
   a closed end that is disposed between the mouth and the proximal aperture and that comprises a curved outline; and
   a region that is disposed between the mouth and the closed end and that is narrow relative to the mouth and the end,
  wherein the mouth of the slot is distal to the region of the slot and is distal to the closed end of the slot, and
  wherein the mouth of the slot is bent into the interior space with operability for retention of the flanges of different sizes and geometries.

2. The apparatus of claim 1, wherein the floor comprises a crease,
 wherein the crease is distal to the closed end of the slot and is distal to the region of the slot,
 wherein the crease extends into the slot on opposing lateral sides of the slot and comprises a bend in the floor where the mouth of the slot is bent into the interior space, and
 wherein distal to the crease, the mouth of the slot projects into the interior space that is occupied by the thumb when the member is worn on the thumb.

3. The apparatus of claim 1, wherein the member comprises:
a distal edge adjacent the distal aperture;
a proximal edge adjacent the proximal aperture;
a first corner that extends longitudinally from the distal edge to the proximal edge; and
a second corner that extends longitudinally from between the first distal edge to the second proximal edge,
wherein the floor of the section extends longitudinally from between the distal edge to the proximal edge and extends laterally from the first corner to the second corner,
wherein the section comprises a first end and a second end,
wherein the first end of the section extends from the first corner away from the floor and towards the second end of the section and partially circumscribes the interior space; and
wherein the second end of the section that extends from the second corner away from the floor and towards the first end of the section and partially circumscribes the interior space,
wherein the member is configured so that when the member is worn on the thumb with the thumb disposed in the interior space, the floor is disposed adjacent a palmar surface of the thumb, the first end extends partially about the thumb, and the second end extends partially about the thumb,
wherein the palmar surface of the thumb comprises a distal palmar surface that extends distally from an interphalangeal joint of the thumb with longitudinal curvature, and
wherein the interior surface of the floor is curved longitudinally between the proximal edge and the distal edge in correspondence with the longitudinally curvature of the distal palmar surface of the thumb.

4. The apparatus of claim 3, wherein the distal edge comprises a first distal edge portion and a second distal edge portion that are disposed on opposite lateral sides of the slot, that are distal to the closed end of the slot, and that are distal to the region of the slot,
wherein the slot extends longitudinally such that a centerline bisects the slot, the slot comprising a first lateral edge and a second lateral edge that extend longitudinally on opposite sides of the centerline,
wherein the mouth of the slot comprises a first section of the formed sheet of malleable metal and a second section of the formed sheet of malleable metal, the floor comprising the first and second sections of the formed sheet of malleable metal,
wherein the first section of the formed sheet of malleable metal forms the first distal edge portion and the first lateral edge of the slot,
wherein the second section of the formed sheet of malleable metal forms the second distal edge portion and the second lateral edge of the slot,
wherein the first section of the formed sheet of malleable material comprises a first crease line that extends from the first distal edge portion to the first lateral edge of the slot and that is diagonal to the centerline of the slot,
wherein the second section of the formed sheet of malleable material comprises a second crease line that extends from the second distal edge portion to the second lateral edge of the slot and that is diagonal to the centerline of the slot,
wherein as the first crease line and the second crease line extend towards the slot, the first crease line and the second crease line converge, and
wherein the first crease line and the second crease line comprise a margin where the mouth of the slot is bent into the interior space.

5. The apparatus of claim 4, wherein the interior surface of the floor provides a space configured to receive the flanges of different sizes and geometries, and wherein the crease line comprises an abrupt bend in the floor.

6. The apparatus of claim 4, wherein the sheet of malleable metal is sufficiently malleable so the medical practitioner can form the member by hand for an individualized fit to the thumb of the medical practitioner.

7. The apparatus of claim 4,
wherein the first end comprises at least two first apertures,
wherein the second end comprises at least two second apertures, and
wherein the at least two first apertures and the at least two second apertures extend through the formed sheet of malleable material, are open, and are configured so that when the ring is worn on the thumb covered by a medical glove, the medical glove protrudes into the at least two first apertures and the at least two second apertures to help hold the ring on the thumb.

8. The apparatus of claim 7,
wherein a first segment of the distal edge of the member extends from the first corner along the first end as the first end partially circumscribes the interior space, wherein with increasing extension from the first corner, the first segment of the distal edge curves proximally, towards the proximal edge, and then distally, away from the proximal edge, and
wherein a second segment of the distal edge of the member extends from the second corner along the second end as the second end partially circumscribes the interior space, wherein with increasing extension from the second corner, the second segment of the distal edge curves proximally, towards the proximal edge, and then distally, away from the proximal edge.

9. The apparatus of claim 7, wherein the member is configured for one-handed aspiration of the hypodermic syringes by the medical practitioner,
wherein the interior surface of the floor is operable to maintain pressure between the thumb and the flanges of different sizes and geometries during said one-handed aspiration,
wherein the first end extends longitudinally between the distal and proximal edges and comprises:
a first end portion adjoining the first corner and extending a first longitudinal distance from the distal edge to the proximal edge;
a second end portion comprising the at least two first apertures and extending a second longitudinal distance from the distal edge to the proximal edge; and
a third end portion disposed between the first end portion and the second end portion and extending a third longitudinal distance from the distal edge to the proximal edge, wherein the third longitudinal distance is less than the first longitudinal distance and is less than the second longitudinal distance, and
wherein the second end extends longitudinally between the distal and proximal edges and comprises:
a fourth end portion adjoining the second corner and extending a fourth longitudinal distance from the distal edge to the proximal edge;

a fifth end portion comprising the at least two second apertures and extending a fifth longitudinal distance from the distal edge to the proximal edge; and a sixth end portion disposed between the fourth end portion and the fifth end portion and extending a sixth longitudinal distance from the distal edge to the proximal edge, wherein the sixth longitudinal distance is less than the fourth longitudinal distance and is less than the fifth longitudinal distance.

10. An apparatus for aiding usage of hypodermic syringes having plungers with flanges of different sizes and geometries that different manufacturers produce, the apparatus comprising:

a ring that is formed of a sheet of malleable metal, that is configured for wearing on a thumb of a user, and that comprises:

a distal edge defining a distal aperture configured to extend circumferentially about a distal portion of the thumb when the ring is worn on the thumb;

a proximal edge defining a proximal aperture longitudinally displaced from the distal aperture and configured to extend circumferentially about a proximal portion of the thumb when the ring is worn on the thumb, wherein the proximal aperture is larger than the distal aperture and the ring tapers from the proximal edge to the distal edge;

a section extending longitudinally between the distal aperture and the proximal aperture and extending circumferentially to define an interior space, the section comprising:

a first corner and a second corner, each extending longitudinally from the distal edge to the proximal edge;

a floor extending laterally from the first corner to the second corner and longitudinally from the distal edge to the proximal edge and comprising an interior surface facing the interior space; and a slot that is disposed in the floor and that comprises a closed end and a mouth, the mouth formed in the distal edge of the ring adjacent the distal aperture of the ring, the slot extending from the mouth towards the proximal aperture to the closed end, wherein the mouth of the slot is bent into the interior space with operability for retention of the flanges of different sizes and geometries, wherein the floor comprises a crease where the mouth of the slot is bent into the interior space, wherein the crease extends across the slot adjacent the distal aperture, wherein the crease is distal to the closed end of the slot, and wherein the mouth of the slot projects into the interior space distal to the crease, and wherein the interior surface of the floor slopes upward from the proximal edge to the distal edge to accommodate a contour of the thumb.

11. The apparatus of claim 10, wherein the interior space comprises dimensions for accommodating the thumb of the user and the flanges of different sizes and geometries that different manufacturers produce, with interior contours of the ring following contours of the thumb, wherein the section further comprises:

a first end that extends from the first corner partially about the interior space and that comprises at least one open aperture extending through the formed sheet of malleable metal; and a second end extending from the second corner partially about the interior space and that comprises at least one other open aperture extending through the formed sheet of malleable metal.

12. The apparatus of claim 11, wherein the slot narrows proximal to the crease, between the closed end and the mouth.

13. The apparatus of claim 12, wherein the malleable metal comprises silver.

14. An apparatus for fastening a plunger of a hypodermic syringe to a thumb of a medical practitioner for one-handed aspiration, the apparatus comprising a member that is configured to extend at least partially around the thumb of the medical practitioner when worn by the medical practitioner as a ring, the member comprising:

a distal edge that is configured to extend about a distal location of the thumb and that defines a distal aperture;

a proximal edge that is configured to extend about a proximal location of the thumb, wherein the proximal edge defines a proximal aperture that is larger than the distal aperture, wherein the member tapers from the distal edge to the proximal edge to accommodate shape of the thumb between the distal and proximal locations of the thumb and to promote a snug fit when the member is worn by the medical practitioner;

a first corner extending from the distal edge to the proximal edge;

a second corner extending from the distal edge to the proximal edge;

a floor that extends laterally from the first corner to the second corner, that extends longitudinally from the proximal edge to the distal edge while sloping upward to accommodate contour of the thumb, and that is configured for disposing adjacent a palmar surface of the thumb when the member is worn by the medical practitioner;

a first upper portion that extends longitudinally between the distal and proximal edges, that extends from the first corner over the floor and towards a second upper portion, and that is configured for extending adjacent a dorsal surface of the thumb when the member is worn by the medical practitioner;

the second upper portion that extends longitudinally between the distal and proximal edges, that extends from the second corner over the floor and towards the first upper portion, and that is configured for extending adjacent the dorsal surface of the thumb when the member is worn by the medical practitioner; and a slot that is disposed in the floor between the first and second corners, that extends from the distal edge towards the proximal edge, and that is sized to receive a shaft of the plunger and to impede passage of a flange of the plunger, the slot comprising:

a mouth formed in the distal edge and comprising a first width;

a closed end comprising a curved outline that comprises a second width; and a region that is disposed between the mouth and the closed end and that comprises a third width, wherein the third width is narrower than the first width and is narrower than the second width, wherein the distal edge comprises:

a first distal edge portion that extends from the first corner along the first upper portion, wherein with increasing separation from the first corner, the first distal edge portion curves towards the proximal edge and then away from the proximal edge; and a second distal edge portion that extends from the second corner along the second upper portion, wherein with increasing separation from the second corner, the second distal edge portion curves towards the proximal edge and then away from the proximal edge, wherein the floor, the first upper portion, and the second upper portion define an interior space for receiving the thumb when the member is worn, and wherein the mouth of the slot is bent into the interior space at a crease in the floor that extends through the slot, that is distal to the closed end of the slot, and that is distal to the region of the slot.

15. The apparatus of claim 14, wherein the floor comprises an interior surface that is contoured to provide a space between the floor and the thumb that accommodates the flange across a range of flange sizes and geometries as produced by different hypodermic syringe manufacturers.

16. The apparatus of claim 15, wherein the interior surface of the floor is contoured to seat the flange when the flange is disposed between the floor and the thumb with the shaft extending through the slot adjacent the curved outline.

17. The apparatus of claim 16, wherein the first upper portion curves over the floor, wherein the second upper portion curves over the floor, wherein the palmar surface of the thumb comprises a friction ridge region that extends laterally on the thumb between a first friction ridge margin and a second friction ridge margin, wherein the member is configured so that when the member is worn by the medical practitioner, the first corner is disposed adjacent the first friction ridge margin and the second corner is disposed adjacent the second friction ridge margin, and wherein the member is configured to, when worn by the medical practitioner with said snug fit, fasten the flange between the interior surface of the floor and the friction ridge region, with the shaft extending through the slot adjacent the curved outline.

\* \* \* \* \*

UNITED STATES PATENT AND TRADEMARK OFFICE
CERTIFICATE OF CORRECTION

PATENT NO. : 10,973,982 B2  
APPLICATION NO. : 16/827433  
DATED : April 13, 2021  
INVENTOR(S) : Virginia Souris Keating Page 1 of 1

It is certified that error appears in the above-identified patent and that said Letters Patent is hereby corrected as shown below:

In the Claims

Column 20, Claim 1, Lines 49-51: "a region that is disposed between the mouth and the closed end and that is narrow relative to the mouth and the end" should read -- a region that is disposed between the mouth and the closed end and that is narrow relative to the mouth and the closed end --

Column 21, Claim 3, Line 35: "longitudinally curvature" should read -- longitudinal curvature --

Column 22, Claim 5, Lines 9-10: "wherein the crease line comprises" should read -- wherein the crease lines comprise --

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*